United States Patent [19]
Speirs et al.

[11] Patent Number: 6,011,199
[45] Date of Patent: Jan. 4, 2000

[54] METHOD FOR PRODUCING FRUITING PLANTS WITH IMPROVED FRUIT FLAVOUR

[75] Inventors: James Speirs, Chapham; Elizabeth Lee, Myrtle Bank; Terrence James Longhurst, Mt. Colah; Richard Hinde, Thornleigh; Colin John Brady, Shoal Bay, all of Australia

[73] Assignees: Commonwealth Scientific; Industrial Research Organisation, both of Campbell, Australia

[21] Appl. No.: 08/937,610

[22] Filed: Sep. 25, 1997

Related U.S. Application Data

[63] Continuation-in-part of application No. 08/448,600, Jul. 26, 1995, Pat. No. 5,821,398.

[30] Foreign Application Priority Data

Dec. 15, 1992 [AU] Australia ................................ PL6349
May 26, 1993 [AU] Australia ................................ PL9059
Aug. 19, 1993 [AU] Australia ................................ PM0712
Aug. 19, 1993 [AU] Australia ................................ PM0713
Aug. 13, 1997 [AU] Australia ................................ PO8533
Sep. 27, 1999 [AU] Australia ................................ PO2662

[51] Int. Cl.$^7$ .......................... C12N 15/29; C12N 15/82; A01H 5/00; A01H 5/08
[52] U.S. Cl. .......................... 800/278; 800/287; 800/290; 800/298; 800/317.4; 435/69.1; 435/320.1; 435/468; 536/23.6
[58] Field of Search ..................... 536/23.6; 435/172.3, 435/320.1, 468, 69.1; 800/205, 200, 278, 287, 290, 298, 317.4

[56] References Cited

PUBLICATIONS

Van der Straeten et al. Tomato alcohol dehydrogenase expression during fruit ripening and under hypoxic conditions. FEBS Letters. 295 (1–3):39–42, Dec. 1991.

Genez et al. Isolation of a tomato alcohol dehydrogenase 2–encoding cDNA using phage–promoted antibody screening of a plasmid cDNA library. Gene. 123:157–164, Jan. 1993.

Longhurst et al. Structure of the tomato Adh2 gene and Adh2 pseudogenes, and a study of Adh2 gene expression in fruit. Plant Molecular Biology. 26:1073–1084, Nov. 1994.

Kazeniac et al. J. Food Science 35:519–530, 1970.

*Primary Examiner*—David T. Fox
*Attorney, Agent, or Firm*—McDermott, Will & Emery

[57] ABSTRACT

A method for producing a transformed fruit plant which produces ripened fruit with improved flavor as compared to ripened fruit produced by its parental plant, said method comprising;

stably transforming explants of said parental plant with at least one DNA molecule comprising a nucleotide sequence encoding alcohol dehydrogenase II (ADH2) or a functional portion thereof operably linked to a suitable promoter sequence, such that transformed fruit plants grown from said explants express said DNA molecule(s) in fruit tissue, and selecting a transformed fruit plant which produces ripened fruit with improved flavor as compared to ripened fruit produced by said parental plant.

20 Claims, 14 Drawing Sheets

(SEQ ID NO:1)
→
AAATATCCACTGCCTCAACTGAGTAAACAACCAAATTTGTGTTCTATAAAAAGTTTCATAT

TTAGTGATCACTAAAAAAAATCAAGAGAAGATGTCGACTACTGTAGGCCAAGTCATTCGTTGCA
(SEQ ID NO:2)→ M  S  T  T  V  G  Q  V  I  R  C  K

AAGCTGCTGTGGCATGGGAGGCTGGTAAGCCATTAGTGATGGAGGAAGTGGATGTTGCTCCTC
 A  A  V  A  W  E  A  G  K  P  L  V  M  E  E  V  D  V  A  P  P

CACAGAAAAATGGAAGTTCGTCTTAAGATCCTCTACACTTCACTCTGTCATACTGATGTATACT
 Q  K  M  E  V  R  L  K  I  L  Y  T  S  L  C  H  T  D  V  Y  F

TCTGGGAAGCTAAGGTCAAAATCCAGTCTCTTCCTCGAATTCTTGGACATGAAGCAGCAGGGA
 W  E  A  K  G  Q  N  P  V  F  P  R  I  L  G  H  E  A  A  G  I

TTTGTGGAGAGTGTTGGAGAGGGAGTAACAGACCTTGCACCAGGAGACCATGTTCTTCCTGTCT
 V  E  S  V  G  E  G  V  T  D  L  A  P  G  D  H  V  L  P  V  F

TTACAGGGAATGTAAAGATTGCGCTCACTGTAAATCTGAAGAAAGCAATATGTGTAGCCTCT
 T  G  E  C  K  D  C  A  H  C  K  S  E  E  S  N  M  C  S  L  L

FIG. 1a-1 Tomato Adh2 cDNA

```
                  450        459        468        477        486        495        504
           TAAGGATTAACACTGACAGGGGAGTGATGCTTAATGATGGAAAATCAAGATTTCCATCAATG
            R  I  N  T  D  R  G  V  M  L  N  D  G  K  S  R  F  S  I  N  G 513        522        531        540        549        558        567
           GAAACCCCATTTACCATTTGTTGGGACCTCTACTTTTAGTGAGTACACCGTGGTTCATGTTG
            N  P  I  Y  H  F  V  G  T  S  T  F  S  E  Y  T  V  V  H  V  G 576        585        594        603        612        621        630
           GATGTGTTGCAAAAATTAACCCCTCTTGCTCCTCTTGACAAAGTATGTGTCCTTAGTGTGGAA
            C  V  A  K  I  N  P  L  A  P  L  D  K  V  C  V  L  S  C  G  I 639        648        657        666        675        684        693
           TTTCGACAGGCCTTGGAGCAAGTTTGAATGTTGCTAAACCAACAAAAGGCTCAAGTGTGGCTA
            S  T  G  L  G  A  S  L  N  V  A  K  P  T  K  G  S  S  V  A  I 702        711        720        729        738        747        756
           TATTTGGACTAGGAGCTGTAGGCCCTCGCGGCTGCAGAAGGAGCCAGAATTGCTGGTGCCTCGA
            F  G  L  G  A  V  G  L  A  A  A  E  G  A  R  I  A  G  A  S  R 765        774        783        792        801        810        819
           GGATAAATTGGTGTTGATTTAAATGCTAGTAGATTTGAGCAAGTAAGAAATTGGTGTGACAG
            I  I  G  V  D  L  N  A  S  R  F  E  Q  A  K  K  F  G  V  T  E 828        837        846        855        864        873        882
           AGTTTGTGAACCCAAAGGACTATAGTAAACCAGTTCAAGAGGTAATTGCTGAGATGACTGATG
            F  V  N  P  K  D  Y  S  K  P  V  Q  E  V  I  A  E  M  T  D  G 891        900        909        918        927        936        945
           GCGGAGTCGATAGGAGTGTGGAATGTACTGGTCACATTGATGCTATGATTTCAGCATTTGAAT
            G  V  D  R  S  V  E  C  T  G  H  I  D  A  M  I  S  A  F  E  C
```

FIG. 1a-2

```
                954         963         972         981         990         999        1008
       GTGTCCATGATGGCTGGGGAGTGGGCGGTTCTTGTTGGTGTACCCCATAAAGAAGCTGTGTTCA
        V   H   D   G   W   G   V   A   V   L   V   G   V   P   H   K   E   A   V   F   K 1017        1026        1035        1044        1053        1062        1071
       AGACACATCCTCTGAACTTTTGAATGAACGGACTCTCAAAGGAACCTTCTTTGGAAACTACA
        T   H   P   L   N   F   L   N   E   R   T   L   K   G   T   F   F   G   N   Y   K 1080        1089        1098        1107        1116        1125        1134
       AACCTCGTTCGGATATTCCTTGTGTTGAGAAATACATGAACAAAGAACTTGAATTGGAGA
        R   S   D   I   P   C   V   V   E   K   Y   M   N   K   E   L   E   L   E   K 1143        1152        1161        1170        1179        1188        1197
       AATTCATCACTCATACACTTCCATTTGCTGAAATCAATAAGGCTTTCGATTTAATGCTGAAGG
        F   I   T   H   T   L   P   F   A   E   I   N   K   A   F   D   F   M   L   K   G 1206        1215        1224        1233        1242        1251        1260
       GAGAAGGCCTTCGTTGCATCATCACCATGGCGGACTAAACTTTCTGTCCTAGAAAAGGAGCTT
        E   G   L   R   C   I   I   T   M   A   D   *

1269        1278        1287        1296        1305        1314        1323
       CTACTGTTTGAGAAAAAGACCAATAAATTGTCACTGTCTTATTTTCCCTTTCGTGTTTGGTT 1332        1341        1350        1359        1368        1377        1386
       GAGTTGTAACATTCCATCCATGTCTCTCTTTGTCTTTTGCTTAGATGTTGTGCTTTGCCAT 1395        1404        1413        1422        1431        1440        1449
       ATCTCTTTTCGATTCTTGTAAAAAATGCAAATTCTCTCTGTTTTATCTCAAGTATATTTACAGA 1458        1467        1476        1485        1494        1503        1512
       ATTTCAGTGATTGATAAATCTAAACTTTATCATAATATAATCCAAACAGAATTTCAATTGAA

AAAAAAAA
```

FIG. 1a-3

(SEQ ID NO:3)
↓
Genomic  GATCAAAAGATGAACTAAGGATAATATTTTTGATATTTTACCTTTTT

TTTAATTATAACGTTGTTAAGATATCAAAGGACCAATTATAAGAAAACCACCC  -842

AAAGGTTTCATGTTTTGATTGAAAAAACCATCAAACAACGCAATACAACTGCTC

AACTAGAATCAACATAACAAAAAAATATACTTAATGAGATCATTTATAACCTA  -735

AATTATAACCCCTCCGTGCACTTTCATTTATCATGTTATATTTTACGCAAGTCA

ATTTGATTCATTTTAAAAGTTAAATGAGATTATATTAATTTAATATTTTAAAT  -628

AAAATTTTCAGATATTTAAAAATTATATGAAAGTATCATGAATTGTAGTTTTT

TTTTGCATATATGAAAAAATACATTATAAATATTAGTCAATTTTTTTATAATT  -521

TGACTCTAAATATGAAAAAAATGACAATTAAAAATAGACGGAGGTTGTAAATT

AGCTTATTAATTATTAATTTGATAAATATCATAATTAACTGATAATGACAATT  -414

AAATATTTAGAAGACGATAATGACAGAAATCAACGTTATTTTAGGTATAATTTT

TGTTGTATTTTTGAAAAAAATAATCTTTTTTCTGCAACTGGTTATATTAAGTG  -307

AACAAACAAAAAACAAGTAGTATAAAAAAATTACAAGTGGACATAAAACAAAT

GAGATACAGTATTTGTGTTTCCATTGGAATATTAGCTTGACAAAAACTCAAAC  -200

GAGCAACACAAAACAAACAGCTAAAAAACCTGTTTTGAAAAATCCAGTGACCAA

AACATGTAAATGGTTTTACTGTGGCCTATTGTTTTTTCACCTTTCCCAATTAT  -93

(SEQ ID NO:4)
↓
cDNA   AAATATCCACTGCCTCAACTGAGTAAACAACCAAAATTTGTGTTCTATAAAAG
       AAATATCCACTGCCTCAACTGAGTAAACAACCAAAATTTGTGTTCTATAAAAG (SEQ ID NO:5) → M  S  T  T  V
cDNA   TTTTCATATTTAGTGATCACTAAAAAAAAATCAAGAAGATGTCGACTACTGTA
       TTTTCATATTTAGTGATCACTAAAAAAAAATCAAGAAGATGTCGACTACTGTA     15
                                             -GA1693

G  Q  V  I  R  C  K
cDNA   GGCCAAGTCATTCGTTGCAAAG
       GGCCAAGTCATTCGTTGCAAAGGTATAATAATTCCATGATTCTGTAATTTCCTC

FIG. 1b-1  Tomato Adh2 Gene Sequence with cDNA

```
                 Intron 1                      (SEQ ID NO:7) → A
cDNA                                           (SEQ ID NO:6) → C
        GTTTTTTTTTTAAGTTTGATAATTTTTGTGGTAATTATATATTATTTATAGC       122

A  V  A  W  E  A  G  K  P  L  V  M  E  E  V  D  V  A
cDNA    TGCTGTGGCATGGGAAGCTGGTAAGCCATTAGTGATGGAGGAAGTAGATGTTGC
        TGCTGTGGCATGGGAAGCTGGTAAGCCATTAGTGATGGAGGAAGTAGATGTTGC

P  P  Q  K  M  E  V  R  L  K  I  L  Y  T  S  L  C
cDNA    TCCTCCACAGAAAATGGAAGTTCGTCTTAAGATCCTCTATACTTCACTCTGTC
        TCCTCCACAGAAAATGGAAGTTCGTCTTAAGATCCTCTATACTTCACTCTGTC         229

H  T  D  V  Y  F  W  E  A  K
cDNA    ATACTGATGTATACTTCTGGGAAGCTAAG
        ATACTGATGTATACTTCTGGGAAGCTAAGGTAAACAAAACTAAATTACGGGACT

Intron 2
        ACGTTGAGTATGTTAGTGTTGTCAGCAAATTTTATAAGGGGATTATTTCCTTT.        336

(SEQ ID NO:9) G  Q  N  P  V  F  P  R  I  L  G  H  E  A
cDNA    (SEQ ID NO:8) GGTCAAAATCCAGTCTTTCCTCGAATTCTTGGACATGAAGC
        GAACTGATTTCAGGGTCAAAATCCAGTCTTTCCTCGAATTCTTGGACATGAAGC

A  G                                      Intron 3
cDNA    AGCAGG
        AGCAGGGTATGTGTTATCTTGTTTCAATTGATTGATTTGAATTCATCATTTAC         443

(SEQ ID NO:11) →     I
cDNA                                       (SEQ ID NO:10) → GAT
        TGTTTCTAAAGCTAAAAGGGTACTGAATTTTGTTGTCTTCTTGATATTTAGGAT

V  E  S  V  G  E  G  V  T  D  L  A  P  G  D  H  V
cDNA    TGTGGAGAGTGTTGGAGAGGGAGTAACAGACCTTGCACCAGGAGACCATGTTC
        TGTGGAGAGTGTTGGAGAGGGAGTAACAGACCTTGCACCAGGAGACCATGTTC         550

L  P  V  F  T  G  E  C  K  D  C  A  H  C  K  S  E  E
cDNA    TTCCTGTCTTTACAGGGGAATGTAAAGATTGCGCTCACTGTAAATCTGAAGAAA
        TTCCTGTCTTTACAGGGGAATGTAAAGATTGTGCTCACTGTAAATCTGAAGAAA

S  N  M  C  S  L  L  R  I  N  T  D  R  G  V  M  L  N
cDNA    GCAATATGTGTAGCCTCTTAAGGATTAACACTGACAGGGGAGTGATGCTTAAT
        GCAATATGTGTAGCCTCTTAAGGATTAACACTGACAGGGGAGTGATGCTTAAT         657

D  G  K  S  R  F  G  I  N  G  N  P  I  Y  H  F  V  G
cDNA    GATGGAAAATCAAGATTTTCCATCAATGGAAACCCCATTTACCATTTTGTTGGG
        GATGGAAAATCAAGATTTTCCATCAATGGAAACCCCATTTACCATTTTGTTGGG

T  S  T  F  S  E  Y  T  V  V  H  V  G  C  V  A  K  I
cDNA    ACCTCTACTTTTAGTGAGTACACCGTGGTTCATGTTGGATGTGTTGCAAAAAT
        ACCTCTACTTTTAGTGAGTACACCGTGGTTCATGTTGGATGTGTTGCAAAAAT         764
```

FIG. 1b-2

```
             N  P  L  A  P  L  D  K  V  C  V  L  S  C  G  I  S  T
cDNA  TAACCCTCTTGCTCCTCTTGACAAAGTATGTGTCCTTAGTTGTGGAATTTCGAC
      TAACCCTCTTGCTCCTCTTGACAAAGTATGTGTCCTTAGTTGTGGAATTTCGAC

Intron 4
cDNA  AG
      AGGTATAGACGAAGACAACGATAGATTATGTTACTAGTTTCTTTTTAAGGAGC          871

(SEQ ID NO:13) →  G  L  G  A  S  L  N
cDNA            (SEQ ID NO:12) →  GCCTTGGAGCAAGTTTGAA
      TGCTCAATTGTTGATTGATATGAATACTTTTCCAGGCCTTGGAGCAAGTTTGAA

V  A  K  P  T  K  G  S  S  V  A  I  F  G  L  G  A
cDNA  TGTTGCTAAACCAACAAAAGGCTCAAGTGTGGCTATATTTGGACTAGGAGCTG
      TGTTGCTAAACCAACAAAAGGCTCAAGTGTGGCTATATTTGGACTAGGAGCTG         978

V  G  L  A                                Intron 5
cDNA  TAGGCCTCGCG
      TAGGCCTCGCGGTGAGTATGCTCCGTTGTGTTGTTTTATTGTTTCCCGTATATG (SEQ ID NO:15) →  A  A  E  G  A  R
cDNA            (SEQ ID NO:14) →  GCTGCAGAAGGAGCCAGA
      TGTTAGTCTTACAGATGACTGACTCATTTGGTCAGGCTGCAGAAGGAGCCAGA        1085

I  A  G  A  S  R  I  I  G  V  D  L  N  A  S  R  F  E
cDNA  ATTGCTGGTGCCTCGAGGATAATTGGTGTTGATTTAAATGCTAGTAGATTTGAG
      ATTGCTGGTGCCTCGAGGATAATTGGTGTTGATTTAAATGCTAGTAGATTTGAG

Q                                         Intron 5
cDNA  CAAG
      CAAGGTAATATAAATTTTTCCTTATACATTATCTTAAAATTCCTTAGTAAAAC         1192

(SEQ ID NO:17) →  A  K  K  F  G  V  T
cDNA            (SEQ ID NO:16) →  CTAAGAAATTTGGTGTGACAG
      AACTAATTCATCCATTTTACTTGTATTCTACAGCTAAGAAATTTGGTGTGACAG

E  F  V  N  P  K  D  Y  S  K  P  V  Q  E
cDNA  AGTTTGTGAACCCAAAGGACTATAGTAAACCAGTTCAAGAG
      AGTTTGTGAACCCAAAGGACTATAGTAAACCAGTTCAAGAGGTACTCAAATCA         1299

Intron 7
      TATTTAATTTACTTTAATCGAAGAAGAAAAAAGACAGGTCTGAGTTAATAGTTG (SEQ ID NO:19) →  V  I  A  E  M  T  D
cDNA            (SEQ ID NO:18) →  GTAATTGCTGAGATGACTGA
      ATGTCTTTTCTTGAATTCTGATTATTTGATCAGGTAATTGCTGAGATGACTGA        1406

G  G  V  D  R  S  V  E  C  T  G  H  I  D  A  M  I  S
cDNA  TGGCGGAGTCGATAGGAGTGTGGAATGTACTGGTCACATTGATGCTATGATTTC
      TGGCGGAGTCGATAGGAGTGTGGAATGTACGGGTCACATTGATGCTATGATTTC
```

FIG. 1b-3

```
         A   F   E   C   V   H   D                        Intron 8
cDNA AGCATTTGAATGTGTCCATGATG
     AGCATTTGAATGTGTCCATGATGTATGTTTTCTGTAATCAAATTAATTTCCTT    1513

(SEQ ID NO:21)    →    G   W
cDNA                          (SEQ ID NO:20)    →    GCTG
     AGCTGTATGTTTGCGTTCATCTTAACGAACATTGTTGTATTAACTTTAGGGCTG

G   V   A   V   L   V   G   V   P   H   K   E   A   V   F   K   T
cDNA GGGAGTGGCGGTTCTTGTTGGTGTACCCCATAAAGAAGCTGTGTTCAAGACAC
     GGGAGTCGCGGTTCTTGTTGGTGTACCCCATAAAGAAGCTGTGTTCAAGACAC         1620

H   P   L   N   F   L   N   E   R   T   L   K   G   T   F   F   G   N
cDNA ATCCTCTGAACTTTTTGAATGAACGGACTCTCAAAGGAACCTTCTTTGGAAACT
     ATCCTCTGAACTTTTTGAATGAACGGACTCTCAAAGGAACCTTCTTTGGAAACT

Y   K   P   R   S   D   I   P   C   V   V   E   K   Y   M   N   K   E
cDNA ACAAACCTCGTTCGGATATTCCTTGTGTTGTTGAGAAATACATGAACAAAGAA
     ACAAACCTCGTTCGGATATTCCTTGTGTTGTTGAGAAATACATGAACAAAGAA         1727

L   E   L   E   K   F   I   T   H   T   L   P   F   A   E   I   N   K
cDNA CTTGAATTGGAGAAATTCATCACTCATACACTTCCATTTGCTGAAATCAATAAG
     CTTGAATTGGAGAAATTCATCACTCATACACTTCCATTTGCTGAAATCAATAAG

A   F   D   L   M   L   K   G   E   G   L   R   C   I   I   T   M   A
cDNA GCTTTCGATTTAATGCTGAAGGGAGAAGGCCTTCGTTGCATCATCACCATGGC
     GCTTTCGATTTAATGCTGAAGGGAGAAGGCCTTCGTTGCATCATCACCATGGC         1834

D
cDNA GGACTAAACTTTCTGTCCTAGAAAAGGAGCTTCTACTGTTTGAGAAAAAAGACC
     GGACTAAACTTTCTGTCCTAGAAAAGGAGCTTCTACTGTTTGAGAAAAAAGACC cDNA AATAAATTGTCACTGTCTTATTTTCCCTTTCGTGTTTGGTTGAGTTGTAACAT
     AATAAATTGTCACTGTCTTATTTTCCCTTTCGTGTTTGGTTGAGTTGTAACAT         1941 cDNA TCCATCCATGTCTCTTCTTTTGTCTTTTGCTTAGATGTTGTGCTTTGCCATATC
     TCCATCCATGTCTCTTCTTTTGTCTTTTGCTTAGATGTTGTGCTTTGCCATATC cDNA TCTTTCGATTCTTGTAAAAAATGCAAATTCTCTCTGTTTTATCTCAAGTATAT
     TCTTTCGATTCTTGTAAAAAATGCAAATTCTCTCTGTTTTATCTCAAGTATAT         2048 cDNA TTACAGAATTTCAGTGATTTGATAAATCTAAACTTTATCATAATATAATCCAAA
     TTACAGAATTTCAGTGATTTGATAAATCTAAACTTTATCATAATATAATCCAAA cDNA CAGAATTTCAATTGAAAAAAA
     CAGAATTTCAATTGAAAATGATGAAGCCCTTACCGTCATTGTTCC                 2147
```

METHOD FOR PRODUCING FRUITING PLANTS WITH IMPROVED FRUIT FLAVOUR

CROSS REFERENCE TO RELATED APPLICATION

This application is a Continuation-in-Part of application Ser. No. 08/448,600, filed Jul. 26, 1995, now U.S. Pat. No. 5,821,398.

FIELD OF THE INVENTION

This invention relates to DNA sequences encoding tomato alcohol dehydrogenase II (ADH2) enzyme, and hybrid DNA molecules incorporating such sequences. These hybrid DNA molecules can be used in a method for producing fruiting plants, particularly tomato plants, which produce fruit with improved flavour.

BACKGROUND TO THE INVENTION

In the soft fruit industry (e.g. strawberries, peaches, plums, bananas and tomatoes), substantial losses are incurred during transport, storage and marketing because of the susceptibility of softer fruit to mechanical damage and invasion by microorganisms. To limit such losses, plant breeders have selected lines which are less soft, and for many fruits firm cultivars now dominate national and international trade. Unfortunately, while marketing losses may be lower when fruit is less soft, the firmer lines may have reduced market appeal and also tend to be deficient in flavour.

The flavour of ripe fruit is a function of a number of components including sweetness (sugars), sourness (organic acids) and volatile compounds. A large number of volatiles have been identified as contributing to flavour and aroma (1–8). In ripening tomato fruit, approximately 400 volatile compounds have been found in the ripening fruit (5) but of these only a small number have been identified as important components of flavour and aroma. These include Z-3-hexenal, Z-3-hexenol, 2-E-hexenal, hexanal, 3-methylbutanal, 3-methylbutanol, β-ionone, 1-penten-3-one, 2-isobutylthiazole, 6-methyl-5-hepten-2-one, methyl salicylate, geranylacetone, E-2-heptenal, isobutyl cyanide and 2-phenylethanol (9,10,3), Flavour volatiles are formed by several different pathways such as the deamination and decarboxylation of amino acids (3-methylbutanal (11)) and lipid oxidation of unsaturated fatty acids (hexanal and the hexenals (12)) (FIG. 1).

The tomato alcohol dehydrogenase II enzyme (ADH 2; alcohol:NAD$^+$ oxidoreductase; EC 1.1.1.1) has been implicated in the interconversion of the aldehyde and alcohol forms of these volatiles (13,14). The enzyme has also been shown to accumulate in the fruit during ripening and to have appropriate substrate specificities in vitro (14–16). Further, the activity of ADH2 in ripening tomato fruit appears to be a function of the softness of the fruit. For example, in the typically firm tomato fruit of commercial cultivars, ADH2 activity is low and this may contribute to the perception of poor flavour in these fruit.

The present inventors have sought to improve tomato fruit flavour by increasing the ADH2 activity in ripening tomato fruit through the introduction of an additional ADH2-encoding DNA sequence(s) into the parent plants. This involved, firstly, isolating a cDNA (see FIG. 1A) encoding ADH2 and then transforming tomato plant explants. The present inventors have now produced a number of tomato plants so transformed and have demonstrated significant changes to the ratios of 2-carbon aldehydes to alcohols. Whether directly or indirectly, these changes have altered the aroma and/or flavour of the fruit produced by transformed plants. Thus, transformed fruit plants with altered ADH2 activity may have direct commercial value and provide valuable stocks for breeding programs.

SUMMARY OF THE INVENTION

In a first aspect, the present invention provides a method for producing a transformed fruit plant which produces ripened fruit with improved flavour as compared to ripened fruit produced by its parental plant, said method comprising;

stably transforming explants of said parental plant with at least one DNA molecule comprising a nucleotide sequence encoding alcohol dehydrogenase II (ADH2) or a functional portion thereof operably linked to a suitable promoter sequence, such that transformed fruit plants grown from said explants express said DNA molecule(s) in fruit tissue, and selecting a transformed fruit plant which produces ripened fruit with improved flavour as compared to ripened fruit produced by said parental plant.

By "improved flavour" we refer to any change in the organoleptic qualities of the ripened fruit which is perceived by a statistically significant number of persons within a randomly selected test population as an improvement in fruit flavour.

By "functional portion" we refer to any portion of ADH2 which possesses activity which, directly or indirectly, effects interconversion of the 5-carbon and/or 6-carbon alcohols and aldehydes. Such functional portions, which may be identified by routing deletion analysis/mutagenesis methods, may possess lesser or greater activity than the full-length ADH2.

The transformed plants produced according to the method of the invention show altered ADH2 activity and, consequently, demonstrate altered ratios of aldehyde/alcohol volatiles. It is most preferred that the transformed plants show increased ADH2 activity in ripening fruit resulting in increases in the ratios of alcohols/aldehydes in ripened fruit as compared to the ratios of alcohols/aldehydes of ripened fruit produced by the parental plant (which may show low or substantially nil ADH2 activity).

From taste tests conducted on fruit from transformed tomato plants (described hereinafter), the present inventors have determined that increases in ADH2 activity leading to an increase in the amounts of the volatile alcohols hexanol and Z-3-hexenol in ripened fruit, results in improved fruit flavours. Furthermore, the present inventors have recognised that 1 to 5 (approximate) fold increases in the amounts of these volatiles over that typical of control fruit, favourably influences the flavour of the ripened fruit.

Thus, the step of selecting a transformed fruit plant which produces ripened fruit with improved flavour, preferably involves selecting a transformed fruit plant which produces fruit which, when ripened, show a 1 to 10 fold increase in the amounts of the volatile alcohols hexanol and Z-3-hexenol as compared to ripened fruit of said parental plant.

Preferably, the ripened fruit of the selected transformed fruit plant show a 1 to 5 fold increase in the amounts of the volatile alcohols hexanol and Z-3-hexenol. More preferably, the ripened fruit of the selected transformed fruit plants who a 1.0 to 5.0 fold increase in the amount of hexanol and a 1.5 to 4.0 fold increase in the amount of Z-3-hexenol.

The DNA molecule mentioned in the first aspect may comprise an ADH2 nucleotide sequence corresponding to, or derived from the ADH2 nucleotide sequence of the parental plant species/strain. However, more preferably, the DNA molecule comprises an ADH2 nucleotide sequence corresponding to, or derived from the ADH2 nucleotide sequence of a tomato plant species/strain. Most preferably, the DNA molecule comprises an ADH2 nucleotide sequence which substantially corresponds to the cDNA or genomic sequence shown in FIGS. 1a and 1b.

Suitable promoter sequences for use in the present invention include inducible promoters such as the tomato ADH2 promoter (described in International (PCT) patent application No. PCT/AU93/00654 (WO 94/13797)), or endopolygalacturonase (PG), 1-aminocyclopropane-1-carboxylic acid oxidate or E8 promoters. It is, however, preferred to use a constitutive promoter such as the CaMV 35S promoter or one of the family of SCSV (Subterranean Clover Stunt Virus) promoters contained in the pPLEX vectors (International (PCT) patent application No. PCT/AU95/00552 (WO96/06932)).

Further, the DNA molecule encoding the ADH2 or a functional portion thereof may include enhancer elements (e.g. from the octapine synthase gene of *Agrobacterium tumefaciens*—Ellis, J. G. et al., 1987 EMBO J. 6:11–16) or multiple copies of an anaerobic response element (ARE) (Olive, M. R. et al., 1990 Plant Mol. Biol. 15:593–604).

The plants may be transformed such that they include an additional copy of the ADH2 gene or, alternatively, the native ADH2 gene may be replaced by homologous recombination with a recombinant ADH2 gene which is expressed at modified levels (e.g. through the use of a stronger promoter sequence). In some applications, it may be preferred to transform the parental plant with multiple copies of the said DNA molecule.

Preferably the DNA molecule(s) is stably inserted into the plant genome and will be transferred, via the seed or by clonal propagation, to subsequent generations. Transformation may be via, for example, *Agrobacterium tumefaciens*-mediated transfer or the well known DNA particle gun method.

The pathways of synthesis of volatiles such as the 6-carbon aldehydes and alcohols, some 5-carbon aldehydes and alcohols (for example 3-methylbutanal/ol), and simple aldehydes and alcohols such as ethananl/ol, appear to be generally associated with flavour production in ripening fruit (cf References 1–15 and general reference Biogeneration of Aroma (1986), Parliment T H and Croteau R (eds), ACS Symposium Series 317, American Chemical Society, Washington D.C.). In all these pathways, ADH plays a role in interconversion of the aldehydes and alcohols, the balance of which is important to perceived aroma and flavour. It is therefore anticipated that the method of the invention is generally applicable to fruit plants. It is, however, preferable that the fruit plant is a soft fruit plant such as a strawberry plant, peach tree or plum tree. However, most preferably, the fruit plant is a tomato plant.

The method of the invention thus permits suitable "slow ripening" or "slow softening" fruit cultivars to be transformed with a DNA molecule to enable the production of the aroma/flavour enhancing ADH2 or functional portion thereof. Where a constitutive promoter is used, production of the ADH2 or functional portion thereof would be enhanced in all tissues of the plant including ripening fruit. Where an inducible promoter is used, production of the ADH2 or functional portion thereof can be controllably regulated by, for example, selected temperature or gaseous treatments applied at a late stage in the fruit distribution and marketing chain.

In a specific case, benefits can be envisaged in modifying a slow-ripening tomato cultivar by incorporation of a DNA molecule comprising the ADH2 promoter from tomato, suitable enhances, and the tomato ADH2-encoding nucleotide sequence. During the early stages of distribution after harvesting advantage could be taken of the cultivar's inherent resistance to physical damage, but the promoter could be activated, at a point close to sale, to bring out a flavour akin to that of a fast ripening cultivar.

Northern analysis of ripening fruit of two tomato cultivars has shown that the mRNA for ADH2 is present in low abundance in mature green fruit and increases in abundance through ripening and, particularly, late in ripening, In fruit pericarp tissue exposed to atmospheres with 3% (v/v) oxygen, the ADH2mRNA level increases to a maximum within 8–16 hours, and returns to the basal level within 16 hours of return to air. The mRNA level was sensitive to the oxygen level in the atmosphere, increasing 20 fold in 12% (v/v) oxygen and 100 fold in 3% oxygen. These oxygen levels may reflect appropriate levels for the induction of some inducible promoters in commercial amounts of fruit harvested from transformed plants. Alternative methods for induction may include UV light, low temperatures (e.g. 0°–10° C.) and exposure to some organic acids or gaseous $CO_2$.

In a second aspect, the present invention provides a fruit plant transformed with at least one DNA molecule comprising a nucleotide sequence encoding alcohol dehydrogenase II (ADH2) or a functional portion thereof operably linked to a promoter sequence suitable for expression of the said DNA molecule(s) in fruit tissue, such that the transformed fruiting plant produces ripened fruit with improved fruit flavour as compared to ripened fruit produced by said parental plant.

In a third aspect, the present invention provides reproductive material derived or produced from a fruit plant according to the third aspect.

Such reproductive material may include seed, cuttings or any other part or product of the plant from which another plant can be produced.

In a fourth aspect, the present invention provides fruit produced by a fruit plant according to the second aspect.

The term "substantially corresponds" as used herein in relation to the nucleotide sequence encoding tomato ADH2, is intended to encompass minor variations in the DNA sequence which due to degeneracy in the DNA code do not result in a significant change in the encoded protein. Further this term is intended to encompass other minor variations in the sequence which may be required to enhance expression in a particular system but in which the variations do not result in a decrease in biological activity of the encoded protein.

The terms "comprise", "comprises" and "comprising" as used throughout the specification are intended to refer to the inclusion of a stated component or feature with or without the inclusion of a further component or feature or group of components or features.

The invention will now be further described by way of the following, non-limiting examples and with reference to the accompanying figures.

BRIEF DESCRIPTION OF THE ACCOMPANYING FIGURES

FIG. 1a provides the nucleotide sequence of the tomato ADH2 cDNA, pTADH2 (SEQ ID NO:1).

FIG. 1b provides the nucleotide sequence of the tomato ADH2 gene (SEQ ID NO:3).

FIG. 1c is a digram of the genomic clone lambda 2A3 indicating the location of exons 1 to 9 of the ADH2 gene, the relative positions of the EcoR1 fragments and the 5' region comprising the promoter. The region shown dashed has not been sequenced.

FIGS. 2a–c provide diagrammatic representations of constructs PJR-ADH and PRD-ADH.

Construct PJR-ADH: The tomato ADH2 cDNA was inserted between a CaMV 35S-promoter and a Nos 3' termination sequence (B) ligated into the T-DNA region of the binary vector PRJ (A) described by Smith et al., (21) and derived from Bin 19 (22,23).

Construct PRD-ADH: The tomato ADH2 cDNA was inserted between the promoter and 3' regions of the tomato polygalacturonase gene (C) ligated into the T-DNA region (see also A) in the binary vector PRD. The PRD vector is described by Nicholass et al. (24) and, as with the PJR vector, was derived from Bin 19.

FIG. 3 provides graphical results of ADH specific activities in fruit from transformed plants. ADH activities were determined in pericarp from breaker, 2 days post breaker (Breaker+2) or 7 days post breaker (Breaker+7) fruit from transformed tomato plants. The top two histograms show results for plants transformed with the PJR-ADH construct containing the tomato ADH2 cDNA coupled with the constitutive CaMV 35S-promoter. The bottom two histograms show results from plants transformed with the PRD-ADH construct containing the tomato ADH2 cDNA coupled with the tomato fruit ripening specific PG-promoter. Results are arranged in order of increasing activity in Breaker+7 fruit (right hand histograms), and are indicated in the same order in the left hand histograms. Three fruit were averaged for each data point. Ac in each histogram is a control mean±S.D. obtained from 3 fruit (each control point) from separate, untransformed plants.

FIG. 4 provides graphical results of ADH specific activity in ripening fruit from transformed plants. ADH activities in pericarp tissue are shown for ripening fruit from three transformed plants. Plant C13 was transformed with the ADH2 cDNA coupled with the fruit ripening specific PG-promoter. Plants C20 and C23 were transformed with constructs containing the CaMV 35S-promoter. Control, untransformed fruit data are shown as open histograms. Data from transformed plants are shown as closed histograms. Three fruit were averaged for each data point.

FIG. 5 shows the spectrum of volatiles isolated from headspace above macerated whole fruit tissue. Typical spectrum of compounds detected by GC analysis of headspace volatiles.

FIG. 6 provides graphical results of the aldehyde:alcohol ratios for a number of headspace volatiles from fruit of three ADH-modified plants, compared with ratios for control plants. Ratios of aldehydes to alcohols were determined for individual fruit from each plant and means±S.D. were calculated. The number of fruit sampled in each case is shown in Table 1. Control fruit ratios were determined from pooled ratios of all the control fruit, AC#1, AC#2 and AC#4 (total n=10). Hexenal/ol (1) is the ratio of Z-3-hexenal:Z-3-hexenol. Hexenal/ol (2) is the ratio of Z-3-hexenal+E-2-hexenal:Z-3-hexenol. For statistical analysis the plants were grouped into the four genotypes: C,20, C13, C23 and untransformed controls. The data were non-normal and non-orthogonal. Analysis was therefore carried out on log transformed data to give approximately normality. The fixed effects of the genotypes were then measured using restricted maximum likelihood (REML—from the GENSTAT package). The test statistic for the REML analysis is a $\chi^2$ on 3 degrees of freedom. The critical values of $\chi^2$ are 7.815 for P=0.05 and 11.345 for P=0.01. The probabilities of differences between all four groups being significant are as follows: Hexanal/ol ($\chi^2$=23.1) P<0.001; Z-3-hexenal/ol ($\chi^2$=11.02) P<0.01; Hexenal(3Z+2E)/Hexenol 3Z($\chi^2$=10.94) P<0.01; Z-3-hexenal/E-2-hexenol ($\chi^2$=5.87) ns; Octenal/ol ($\chi^2$=8.39) P<0.05; Citral/Geraniol ($\chi^2$=0.98) ns.

DETAILED DESCRIPTION OF THE INVENTION

Example 1

Isolation of a cDNA Encoding Tomato ADH2

Poly A$^+$ RNA was isolated from pericarp tissue of tomato (cv. de Ruiter 83G38) fruit, 9 days after the first appearance of colour (Breaker+9). A cDNA library was constructed from the poly A$^+$ RNA and was cloned into lambda Gem 11 using the protocol or Promega Ltd. The library was screened by hybridisation with a $^{32}$P-labelled fragment of tomato genomic DNA with sequence homology to ADH genes of pear (Llewellyn et al. J. Mol. Biol. 195:115–127, 1987) potato (Matton et al., Plant Mol. Biol. 14: 775–783, 1990) and maize (Dennis et al. Nucleic Acids Res. 13: 727–743, 1985). Four positive colonies were isolated, phage DNA was purified and cDNA insets were transferred from the phage vector to a plasmid vector pGem 11 (Promega) for sequencing, Sequencing was carried out by the dideoxy-method of Sanger et al. PNAS, USA 784: 5463–5467 (1977) on double stranded DNA using pUC universal and reverse primers and oligonucleotide primers to extend known sequence. The four cDNAs had identical 5' sequences and identical open reading frames encoding a protein of 379 amino acids.

The cDNA hybridised strongly to a 1.8 kb RNA species in RNA from ripe but not from unripe tomato fruit. Similarly, the cDNA hybridised to RNA from tomato seedling roots kept anaerobic overnight, but not to RNA from aerobic roots. In contrast, a BGl11 fragment of tomato genomic of cDNA, which contains regions encoding the tomato ADH1 isozyme and hybridises strongly to ADH1 mRNA but weakly to ADH2 mRNA (Wisman et al. Mol. & Gen. Genet. 226:120–128, 1991), did not hybridise to RNA from either ripe fruit or anaerobic root tissue. Thus it was concluded that the cDNAs isolated from the ripening fruit library, encode a tomato ADH2 enzyme.

Figure 1C:
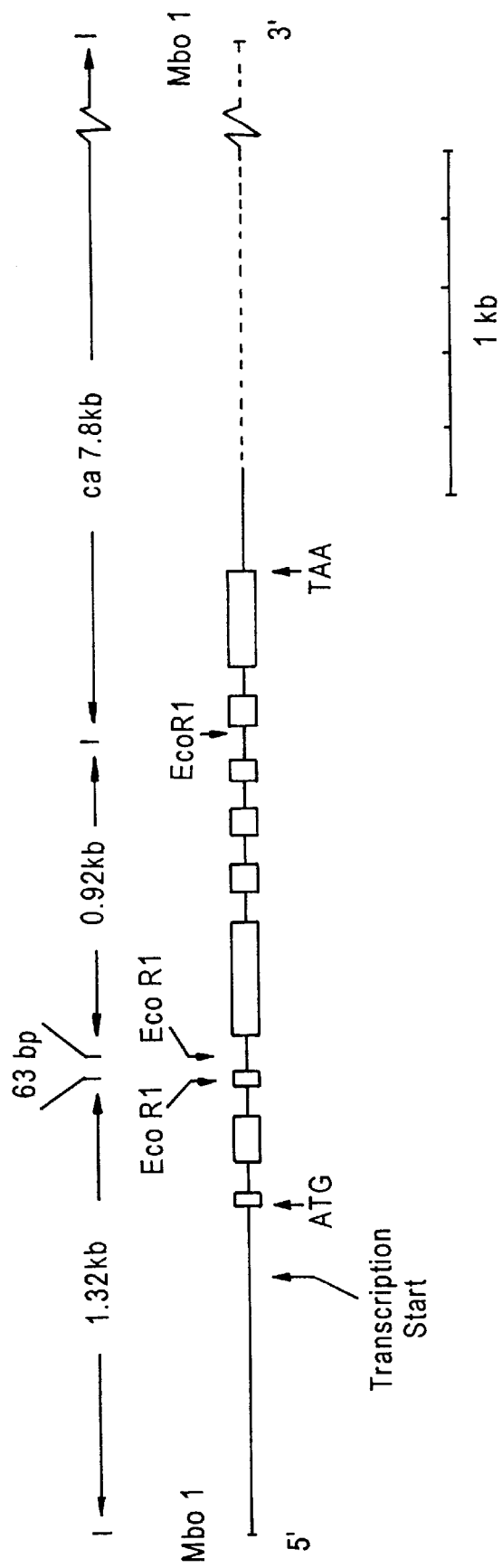

The nucleotide sequence for the cDNA encoding the ADH2 mRNA is provided at FIG. 1a.

The 5' 843 nucleotides of the cDNA including sequence encoding 250 amino acids of the ripening associated ADH2 enzyme provides a particularly useful probe by virtue of its location adjacent to the promoter in the genomic sequence.

Example 2

Isolation of Tomato ADH2 Genomic DNA
Isolation of Tomato Leaf DNA

Young leaves of tomato plants (cv. de Ruiter 83G38) were harvested and snap-frozen in liquid nitrogen. The leaves were ground to a fine powder under liquid nitrogen and DNA was isolated by the method of Thomas et al. Theor. Appl. Genetic 86: 173–180 (1993).
Construction of Genomic Library Aliquots of high molecular weight tomato genomic DNA were digested with varying amounts of MboI restriction endonuclease for 1 hour at 37° C. and digestion was stopped by heating the samples at 75° C. for 10 minutes. The samples were fractionated on a 0.5% agarose gel and the mean size and spread of the digested DNA was determined. 20 µg of genomic DNA as digested with MboI enzyme, under conditions designed to give a fragment size range of between 10 kb and 20 kb, and the reaction was stopped as before. The digested fragments were partially end-filled with dATP and dGTP and were ligated into Lambda GEM-11 XhoI Half-site arms (Promega Corp.), according to the Promega protocols. Three ligations were carried out with arms:fragment ratios of: 0.5 µg:0.25 µg; 0.5 µg:0.5 µg; 0.5 µg:0.75 µg.

The ligated DNA samples were packaged according to Hohn, Methods in Enzymology 68:299–309 (1979) and titred, giving average titres of $1.8 \times 10^5$ pfu/µg arms. The three libraries were pooled.

Library Screening

E. coli, strain KW251 cells, were infected with $2 \times 10^5$ phage, were spread on six, 10 cm×10 cm Luria agar plates (33,000 pfu/plate) and were incubated at 37° C. for 6 hours until small phage plaques had developed. Lifts were taken off the plates onto Biotrace NT nitrocellulose membranes (Gelman Sciences), and the membranes were prehybridised, hybridised and washed according to the Gelman protocols. Dried membranes were exposed to X-ray film (Fuji, RX) with an intensifying screen (Du Pont—Cronex, Lightning-Plus) at −70° C. Hybridisation probes were labelled with $^{32}p$ dATP by oligopriming (Feinberg and Voglestein, Anal. Biochem 132: 6–13, 1983).

Subcloning and Sequencing

The genomic DNA insert of lambda clone 2A3 was digested with EcoR1 restriction enzyme and the resulting fragments subcloned by ligation into the plasmid vector pUC18 (Yanisch-Peron et al., Gene 33: 103–119, 1985) by standard methods.

Double stranded sequencing was carried out by the enzymatic chain-termination method of Sanger et al. Proc. Natl. Acad. Sci. USA 74: 5463–5467 (1977), using universal and reverse M13 primers based on determined sequence.

PCR amplification of the 5' region of the ADH2 gene was carried out on a tomato genomic DNA template using oligonucleotide primers to regions of the ADH2 cDNA as follows:

5' Primer #1078 5' CCACTGCCTCAACTGAG 3'(SEQ ID NO:22)

3' Primer #1057 3' CGACCATTCGGTAATCA 5' (SEQ ID NO:23)

PCR reactions were carried out in 50 µl reactions containing 16.6 mM $(NH)_4SO_4$, 67 mM Tris-HCl pH 8.8, 6.7 mM EDTA, 2 mM $MgCl_2$, 0.15% Triton X-100, 200 µM dNTPs and 200 µg/µl gelatin, with primers added at 22 pmol/µl, 100 ng tomato genomic DNA and 2.5 units of Taq polymerase. Reactions were carried out as follows:

1st cycle
 94° C. 5 mins.
 45° C. 1 min.
 72° C. 1 min.
Followed by 38 cycles as follows:
 94° C. 1 min.
 45° C. 1 min.
 72° C. 1.5 mins.

The PCR product was ligated into pBluescript KS+ vector (Stratagene) linearised at the EcoRV site and T-tailed according to the procedure of Marchuk et al. Nucleic Acids Research 19.1154 (1990).

Results

Duplicate lifts were taken of six plates containing a total $2 \times 10^5$ pfu of a phage library of tomato genomic DNA. The lifts were screened by hybridisation with two probes. The first probe, pADHCR1 was designed to be specific to the 5' end of the tomato ADH2 gene which is expressed in ripening fruit. pADHCR1 was generated by PCR amplification of the genomic sequence bounded by primers #1078 and #1057 defined by the sequence of the ADH2 cDNA and spans exon 1, intron 1 and 34 nucleotides of exon 2 of the ADH2 gene. The second probe, pADH2-3' constitutes the entire ADH2 cDNA 3' of the EcoR1 site at nucleotide 290 on the cDNA (nucleotide 382 on the genomic DNA—Table 1).

Screening with the 5' specific probe, pADHCR1, gave 28 positives. Screening with the 3' specific probe, pADH2-3' gave 20 positives. Only one lambda phage plaque, 2A3, hybridised with both probes, and this plaque was isolated and purified for further characterisation.

EcoR1 digestion of DNA from the lambda genomic clone, 2A3, generated a number of fragments including the left and right arms of the lambda vector and three fragments of insert DNA with sizes of 7.8 kb, 1.4 kb and 1.2 kb. Subsequent subcloning revealed a further insert fragment of 63 bp in size. The EcoR1 fragments were subcloned into pUC18 and were sequenced, allowing alignment of the fragments to be determined (FIG. 1). The 1.4 kb subclone, pADH2-1.4 was found to contain the 5' end of the ADH2 gene, from the EcoR1 site at nucleotide 290 in the cDNA and including introns 1 and 2. The clone includes the transcription start site and extends a further 800 bp upstream encompassing the gene promoter.

The sequence of the clone 2A3 including the ADH2 promoter and the protein-encoding region (including introns) is provided at FIG. 1b. The ADH2 gene has an overall length of 2334 bp from transcription site to poly A addition site.

Example 3

Production of Transformed Tomato Plants Expressing ADH2

Construction of ADH transgenes

The ADH cDNA used for the construction of the ADH transgene, was modified by PCR using the tomato ADH2 cDNA pTADH2 as template (20). The 1.5 Kb ADH2 cDNA includes a 5' untranslated region of 91 bp upstream of the ATG start codon and a 320 bp untranslated region 3' of the TAA stop codon. The integrity of the sequences was confirmed by sequence analysis after modification. Two ADH2 transgenes were constructed. The first construct, PJR-ADH (FIG. 2), consists of the ADH2 cDNA ligated into the binary vector PJR1. The PJR1 vector, described in Smith et al. (21), is a derivative of Bin 19 (22,23) and contains the constitutive CaMV 35S-promoter and the Nos 3' terminator sequence. The second construct, PRD-ADH (FIG. 2), consists of the ADH2 cDNA ligated into the binary vector PRD. The PRD binary vector was derived from Bin 19 and contains the tomato fruit specific PG-promoter (4.8 Kb) and PG-terminator (1.8 kb), (24). The ADH2 cDNA fragment was inserted into the Bsa1 and Spe1 sites of the PRD binary vector.

Tomato Transformation

The constructs PJR-ADH and PRD-ADH were transferred from E. coli DH5α to Agrobacterium tumefaciens LBA4404 by triparental mating via E. coli HB101 and pRK2013. Tomato (Lycopersicum Esculentum Mill cv. Ailsa Craig) transformations were carried out according to Bird et al. (25). Southern analysis of DNA from young leaf tissue was used to estimate the number of NptII and ADH2 inserts integrated into each plant and plants were allowed to grow to maturity and set fruit. Fruit were harvested at first colour change (Breaker, Br) or two days post Breaker (Br+2) and 7 days post breaker (Br+7) and ADH activity in the pericarp tissue was determined.

Genomic Southern Blot Analyses

Genomic DNA was extracted from young leaves by the method of Thomas et al. (26). 7 µg of Hind III digested genomic DNA was fractionated by electrophoresis on 0.7% agarose-TBE gels. The DNA was transferred onto nylon membrane (Zetaprobe, BioRad) as described by the manufacturer. The number of transgene(s) inserted was determined by hybridisation using 32p labelled probes corresponding to the NptII and ADH2 cDNA regions of the transgene. Hybridisation was according to the procedure recommended for Zetaprobe, at 65° C. for 16 h. The filters were washed twice with 2×SSC, 0.1% SDS at 65° C. for 15 min each, followed by two washes of 10 min with 0.1×SSC, 0.1% SDS at 65° C. The membranes were blotted dry and autoradiographed.

Extraction and Assay of ADH

Tomato pericarp tissues, and whole fruit tissues were extracted and assayed according to the method of Longhurst et al. (15). Protein concentration was measured using a protein quantification Kit II (BioRad).

Volatile Analyses

Fruit were harvested 7 days post breaker. 10 g of pericarp tissue was taken from freshly harvested fruit, sliced and then briefly macerated using a Polytron PT2000 homogenizer (Kinematica AG, Switzerland). The slurry was allowed to stand at room temperature for exactly 3 min after which 3.3 g solid $CaCl_2$ were added to inhibit further enzyme activity. 1 µl of uniformly labeled, deuterated Hexanol (80 nmoles/µl) were added as an internal standard. 6.6 g of the mixture was transferred to a 20 ml headspace vial which was sealed with a silicon/teflon septum. The vial was incubated at 40° C. for 30 min. Sampling of the headspace was carried out by insertion of a Solid Phase MicroExtraction (SPME, Supelco) fiber (65 µm Carbowax-Divinylbenzene), for 30 min while continuing incubation of the vial at 40° C. The absorbed sample was analysed by gas chromatography on an HP-GC series 6809 fitted with a capillary DB-wax column, 30 m×0.25 mm ID×0.25 µm) and individual peaks were identified by mass spectrometry. Peak areas were measured by integration and were normalized against the internal deuterated hexanol standard.

Tasting Trial

Tomatoes from each treatment were harvested at between 7 and 9 days into ripening (Breaker+7–9, where Breaker is first colour change). The tomatoes were matched on the basis of size. Each tomato was quartered and the locular tissue, containing the seeds, removed. Each quarter was used for each of the four attributes (ripe flavour, green flavour, sweetness and acidity) by a single panelist.

Four sets of samples were presented to each panelist, each in a different random order. Each set was used to rank only one of the attributes. The order of assessment of the attributes was the same for each panelist (ripe flavour, green flavour, sweetness and acidity).

Panelists were asked to rank the samples on each of the four attributes. Samples with the greatest intensity of the attribute were given a rank of 1, whilst the least intense was ranked 4.

An orthogonal latin square design was used to balance out carry-over effects. This design required 12 assessments. However, due to insufficient samples, only 11 were made in this trial.

Panelists

Seven of the eleven panelists were trained oenologists with extensive experience in wine flavour and acid balance assessment (mean experience=10 years). One panelist whilst not formally trained had three years regular experience in assessing these attributes in wine. Three panelists were CSIRO employees. Whilst all panelists knew the general purpose of the tasting, is a comparison of flavour modified tomatoes, none were aware of the exact nature of the samples.

Results

Transformation with ADH2 constructs and initial screening

Figure 2A:
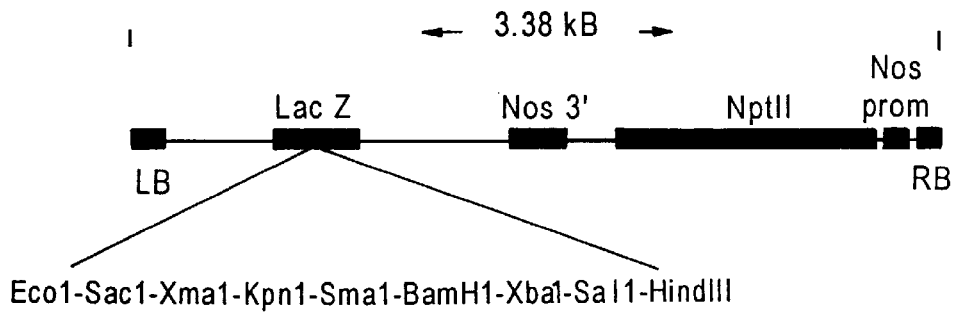
Figure 2B:
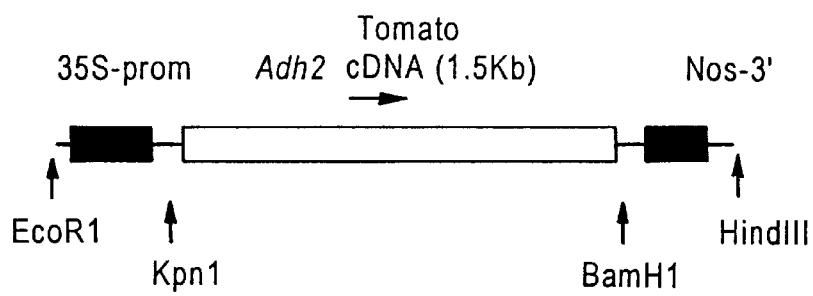
Figure 2C:
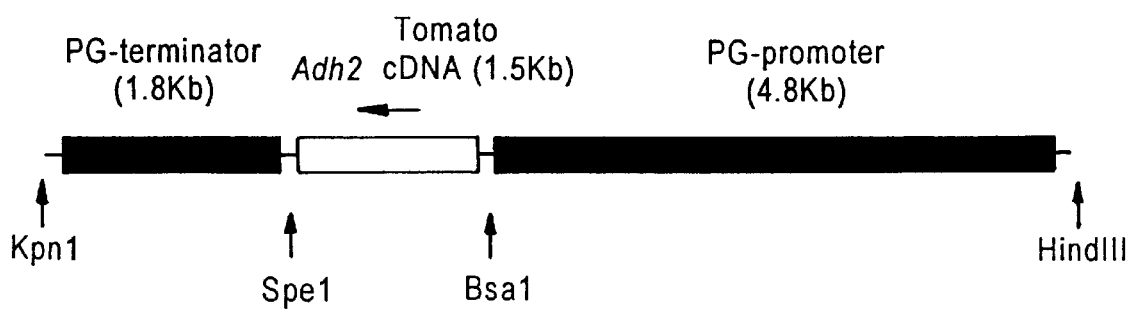
Figure 3A:
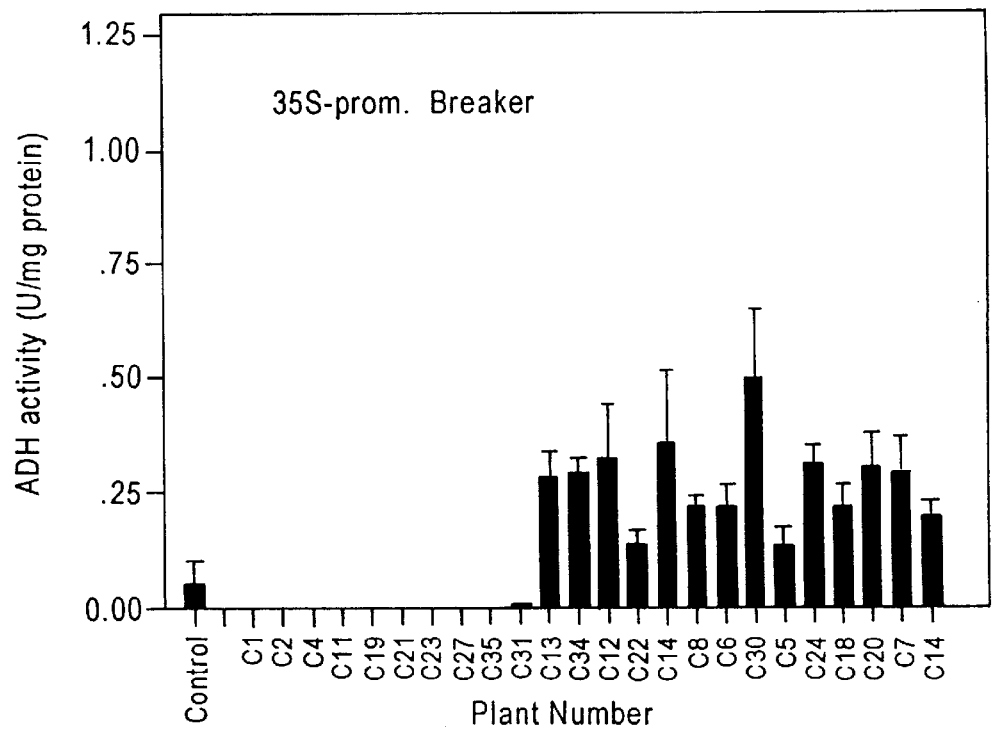
Figure 3B:
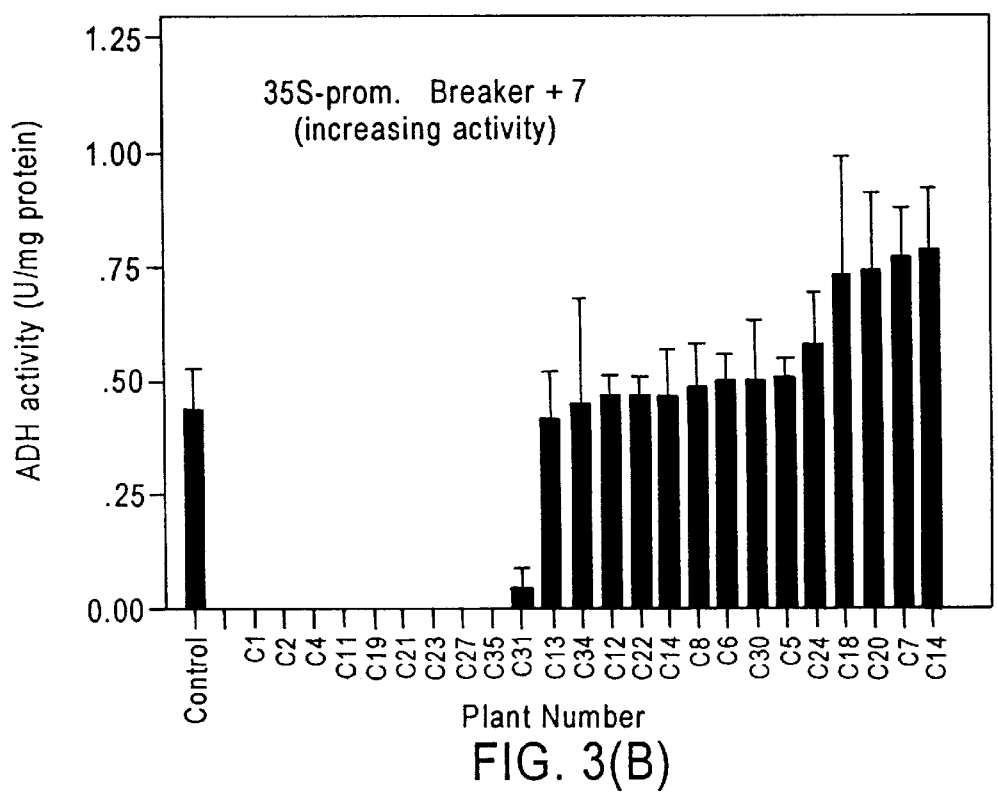
Figure 3C:
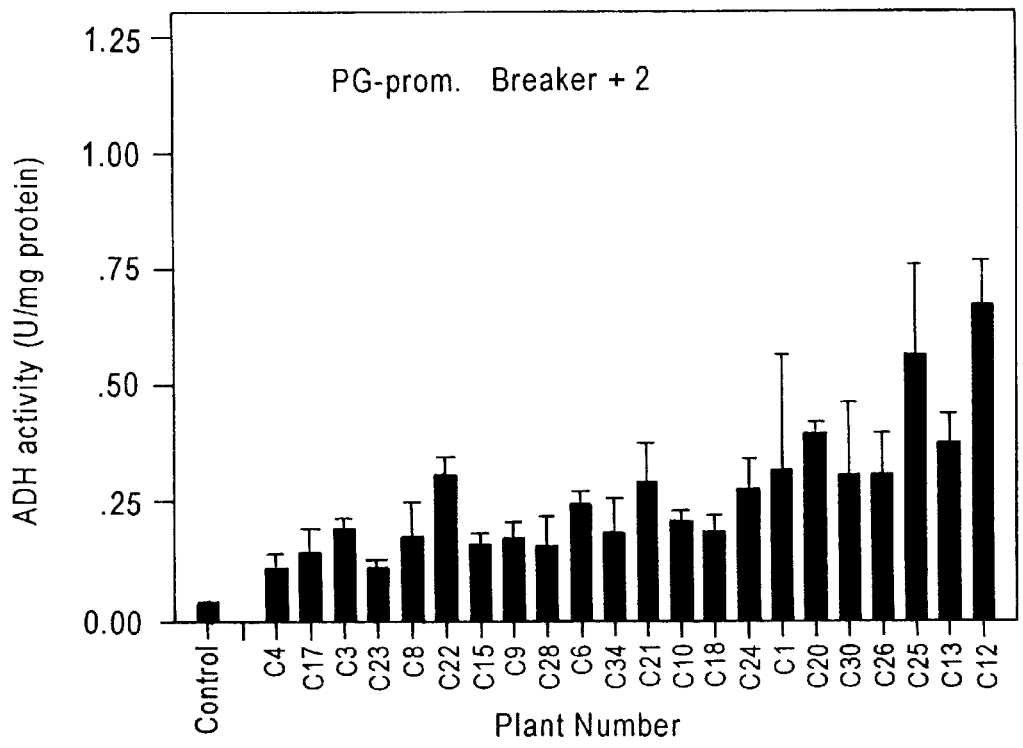
Figure 3D:
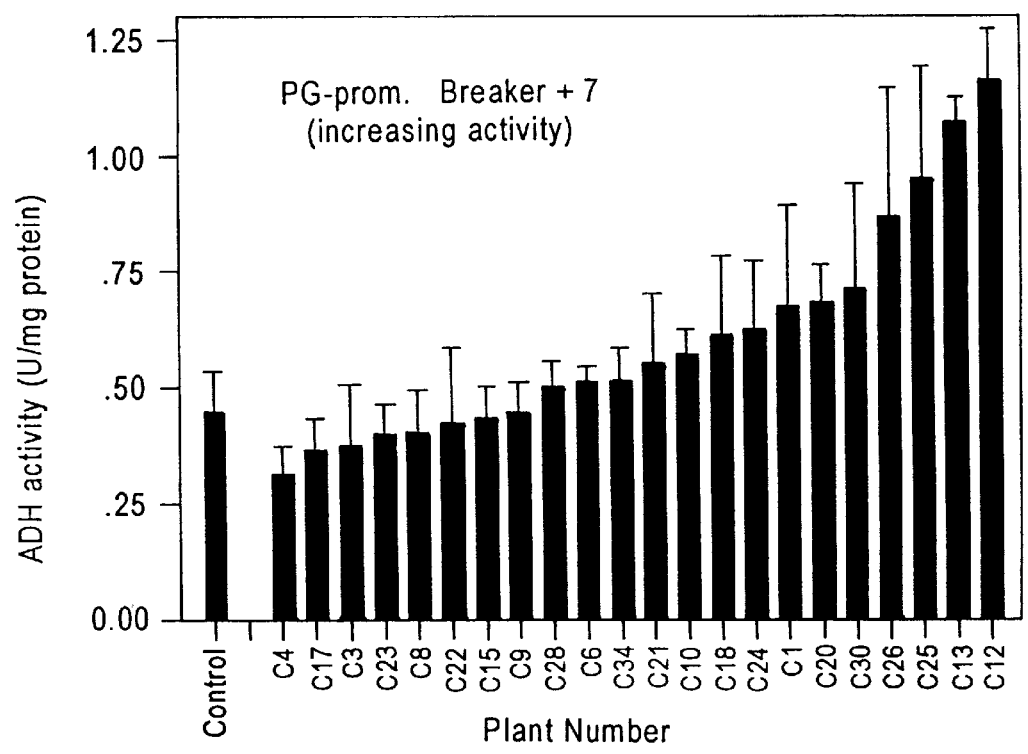

Tomato explants were transformed with constructs containing the tomato ADH2 cDNA as described in FIG. 2, and 30 transformed plants from each experiment were selected.

Two types of transformation construct were used. Both contained the tomato ADH2 cDNA in a sense orientation relative to the construct promoter. In one set of experiments the CaMV 35S-promoter was used to provide constitutive expression of the cDNA. In the other the tomato polygalacturonase gene promoter (25,26) (PG-promoter) was used to provide fruit ripening-specific expression of the cDNA.

Constitutive expression of the introduced cDNA(s) resulted in both enhanced and inhibited accumulation of the ADH2 enzyme in the ripening fruit (FIG. 3). Enhanced levels of accumulation were most evident in Breaker (Br; first colour change) fruit but a number of fruit continued to show significantly ($P<0.05$) enhanced levels at Br+7 (Breaker+7 days). About 40% of the plants analysed had fruit in which ADH2 expression was completely inhibited, presumably by co-suppression.

In the second set of experiments, in which the introduced cDNA(s) were expressed in a fruit ripening-specific manner, ADH activities at Br+2 varied from approximately that in control fruit to a 6–7 times control levels, while activities at Br+7 varied from approximately control fruit levels to 2–3 times control levels (FIG. 3).

ADH activities during ripening

ADH activity was measured in pericarp, locular and whole fruit tissues. Activity was found to vary in the different tissues but was highest in pericarp tissue (data not shown). Because of this, and because of the uniform composition of the tissue, only pericarp activities are presented here.

A small number of plants showing significant modifications in pericarp ADH activities were taken for more extensive analysis during fruit ripening and for analysis of fruit flavour volatiles. Plants C20 and C23 contained constructs with constitutive expression of the inserted cDNA(s). Fruit from these plants showed respectively either enhanced ADH activity or minimal activity in fruit throughout ripening relative to levels in fruit from untransformed control plants (FIG. 4). Plant C13 contained ADH2 cDNAs regulated by the fruit ripening-specific PG-promoter. Fruit from the C13 plant showed significantly enhanced levels of ADH activity which continued to increase up to 7 days post breaker then declined. In a separate series of experiments, ADH levels and volatiles were determined for breaker+7 fruit from these plants and a number of other transformed plants. These data are shown in Table 1.

Analysis of volatiles

Figure 5:
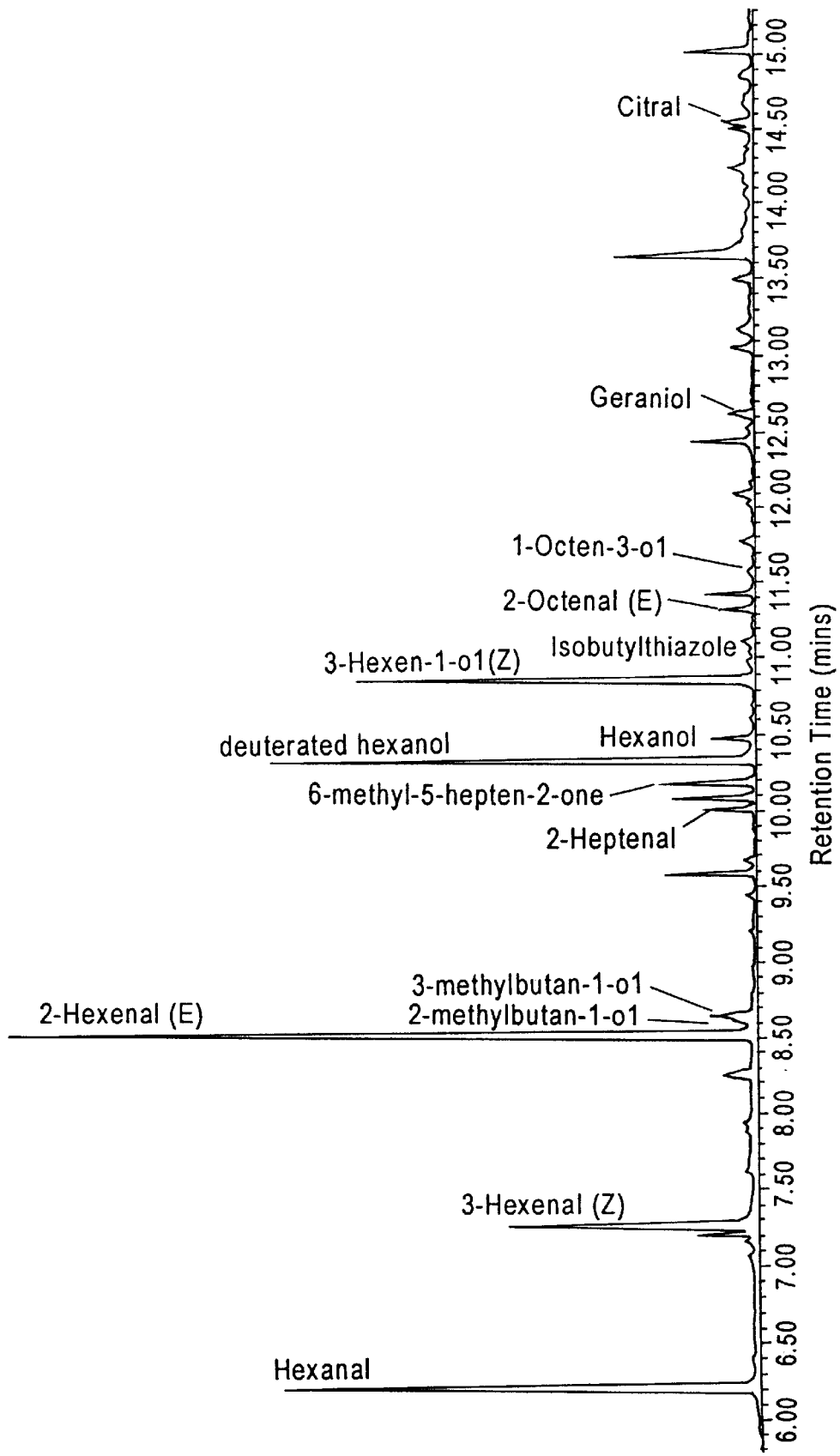

A number of the transformed plants were selected for analysis of volatiles produced in their fruit. Solid Phase Micro Extraction (SPME) was used as a quick and convenient method for measuring headspace volatiles from individual fruit. This method revealed some 15 major peaks of volatiles with many minor peaks (FIG. 5). A number of the volatiles identified in FIG. 5 are amongst those considered to be important to flavour and aroma development. Of particular interest were the hexanal/ol and hexenal/ol compounds, peak areas of which are listed in Table 1, together with areas of some other aldehydes and alcohols detected.

Comparison of areas of individual peaks between tissue from control, high ADH and low ADH fruit showed, in general, little variation. Peak areas of the aldehydes Z-3-hexenal and E-2-hexenal did not vary greatly between the various plants. Similarly the areas of the aldehyde hexanal varied little between plants except in the case of the C13 plant where it was lower, but not significantly different to controls (Table 1). In contrast, levels of the alcohols, hexanol and Z-3-hexenol, did show significant variation between plants with differing ADH levels (Table 1), while E-2-hexenol was not detected in any of the fruit.

:hexenol (3Z) has been included. Hexanal; hexanol, Z-3-hexenal:Z-3-hexanol and the combined hexenal (3Z+2E) :hexenol (3Z) ratios are significantly higher in fruit from the low ADH plant C23 than in fruit from the control plants. In some fruit from C23, no Z-3-hexenol was detectable, resulting in aldehyde to alcohol ratios of infinity. In fruit from the high-ADH plants, C20 and C13, the ratios of aldehyde:alcohol are significantly lower than those of the control fruit.

Included in FIG. 6 are ratios of Octenal:Octenol and Citral:Geraniol, (trans-3,7-dimethyl-2,6-octadien-1-al:trans-3,7-dimethyl-2,6-octadien-1-ol). Ratios of those aldehydes and their alcohols varied from plant to plant but did not show any clear trend related to ADH activity.

Taste characteristics

Results of the taste trial are provided at Table 2. Of the eleven (11) panellists involved in the trial, ten (10) selected the fruit from the constitutive high-ADH plant C20 as

TABLE 1

Number of introduced genes, ADH specific activites and relative abundances of some volatiles in fruit from transformed and control plants.

| | Constitutive promoter High-ADH | | | PG-prom. High-ADH | Controls untransformed | Constitutive promoter Low-ADH | | |
|---|---|---|---|---|---|---|---|---|
| | C7 | C14 | C20 | C13 | AC#1, 2 & 3 | C4 | C11 | C23 |
| Estimated number of genes inserted (Adh2/NptII) | 1/1 | 1/1 | 2/3 | 7/7–8 | — | 3/4 | 2–3/3 | 5/6 |
| Number of fruit sampled | n = 4 | n = 3 | n = 5 | n = 3 | n = 10 | n = 2 | n = 4 | n = 3 |
| ADH specific activity (U/mg protein) | 0.67 ± 0.16* | 0.56 ± 0.04$^{ns}$ | 0.76 ± 0.15** | 1.26 ± 0.31*** | 0.375 ± 0.15 | 0.015 ± 0.02$^{ns}$ | 0.006 ± 0.01** | 0.011 ± 0.02* |
| Hexanal | 8.48 ± 1.60$^{ns}$ | 9.13 ± 0.31$^{ns}$ | 9.94 ± 1.98$^{ns}$ | 6.95 ± 0.89$^{ns}$ | 9.43 ± 1.44 | 9.65 ± 0.88$^{ns}$ | 8.45 ± 0.44$^{ns}$ | 10.09 ± 2.27$^{ns}$ |
| 3-hexenal Z | 8.42 ± 1.07$^{ns}$ | 7.28 ± 0.40$^{ns}$ | 7.73 ± 1.28$^{ns}$ | 7.67 ± 1.42$^{ns}$ | 7.76 ± 1.57 | 9.44 ± 1.51$^{ns}$ | 7.57 ± 0.72$^{ns}$ | 8.71 ± 2.46$^{ns}$ |
| 2-hexenal E | 14.38 ± 3.24$^{ns}$ | 13.57 ± 1.76$^{ns}$ | 15.99 ± 1.72$^{ns}$ | 12.92 ± 2.78$^{ns}$ | 12.37 ± 2.03 | 13.17 ± 0.49$^{ns}$ | 15.88 ± 1.42$^{ns}$ | 10.82 ± 3.23$^{ns}$ |
| Hexanol | 0.25 ± 0.09$^{ns}$ | 0.40 ± 0.05$^{ns}$ | 0.52 ± 0.17*** | 0.29 ± 0.08$^{ns}$ | 0.22 ± 0.07 | 0.029 ± 0.04$^{ns}$ | 0.04 ± 0.02* | 0.02 ± 0.002* |
| 3-hexen-1-ol Z | 3.08 ± 0.28$^{ns}$ | 4.12 ± 0.79$^{ns}$ | 6.02 ± 1.58** | 4.48 ± 1.27* | 2.51 ± 0.46 | 0.25 ± 0.15* | 0.065 ± 0.08*** | 0.057 ± 0.05** |
| Geraniol | 0.72 ± 0.34 | 0.71 ± 0.16 | 0.62 ± 0.14 | 0.49 ± 0.10 | 0.89 ± 0.25 | 0.88 ± 0.09 | 0.6 ± 0.09 | 0.92 ± 0.15 |
| 2-octenal E | 0.43 ± 0.01 | 0.50 ± 0.09 | 0.57 ± 0.06 | 0.45 ± 0.03 | 0.61 ± 0.09 | 0.51 ± 0.07 | 0.52 ± 0.05 | 0.54 ± 0.20 |
| 1-octen-3-ol | 0.09 ± 0.01 | 0.07 ± 0.02 | 0.11 ± 0.02 | 0.08 ± 0.01 | 0.10 ± 0.03 | 0.11 ± 0.03 | 0.10 ± 0.02 | 0.09 ± 0.03 |
| Citral | 0.30 ± 0.10 | 0.90 ± 0.14 | 0.69 ± 0.28 | 0.38 ± 0.10 | 0.70 ± 0.22 | 0.6 ± 0.01 | 0.35 ± 0.07 | 0.44 ± 0.15 |

Number of inserted genes was estimated by quantitating the hybridisation to genomic DNA of probes for Nptil and for Adh2 cDNA. Headspace volatiles were collected by SPME absorption, and analysed by GC/MS. Peak areas were determined by integration and were normalized against the area of a deuterated hexanol standard introduced during maceration of the tissue. Numbers of fruit sampled are indicated (n =). Averaged ADH activites from pericarp tissue and volatile abundances are derived from the same setof fruits, and were derived separately from the data presented in FIG. 3. Statistical comparisons, where shown, were obtained using Tukey-Kramer Comparisons Test (GraphPad InStat package) to compare data in the same row... Data from individual transformed plants were compared with pooled data from the control plants: ns — not significantly different to fruit from control plants (P > 0.05); * — significantly different to fruit from control plants at P < 0.05;  — P < 0.01;* — P < 0.001.

Ratios of the fruit aldehydes to alcohols have been calculated for the plants C20, C13 and C23 and are shown plotted as histograms in comparison with ratios in control fruit (FIG. 6). A statistical comparison of the ratios was also carried out, with the probability of each ratio differing between the four classes of plant, C20, C13, C23 and control, being given in the legend to FIG. 6. As Z-3-hexanal isomerises to E-2-hexenal, the ratio of hexenal (3Z+2E)

having a greater intensity of ripened fruit flavour than the other fruit sampled. This result is statistically significant (0.2% probability of error). The fruit from the constitutive low-ADH plant C23 was generally considered to be bland in flavour, whilst the fruit from the fruit-specific high ADH plant C13 was generally considered as having enhanced aroma but not flavour.

TABLE 2

| | Control untransformed | C23 constitutive low-ADH | C13 fruit specific high-ADH | C20 constitutive high-ADH | P | LSD 5% |
|---|---|---|---|---|---|---|
| Ripe tomato flavour | 28$^b$ | 34$^b$ | 34$^b$ | 14$^n$ | 0.02 | 10 |

TABLE 2-continued

|  | Control untransformed | C23 constitutive low-ADH | C13 fruit specific high-ADH | C20 constitutive high-ADH | P | LSD 5% |
|---|---|---|---|---|---|---|
| Green tomato leaf character | 28[d] | 25[u] | 23[a] | 34[n] | 0.288 | 10 |
| Sweetness | 24[ab] | 32[b] | 36[b] | 16[h] | 0.014 | 10 |
| Acidity | 30[a] | 26[a] | 29[a] | 25[d] | 0.819 | 10 |

Samples with greatest intensity of attribute were given a ranking of 1, while those with least were ranked 4.
Low rank sums imply a high intensity of that attribute.
The lowest rank sum for Ripe Tomato Flavour consisted of ten "1" rankings and a single "4" ranking.

Discussion

By introducing tomato ADH2 cDNA constructs, coupled to either a constitutive promoter or a fruit ripening specific promoter, the present inventors have produced a number of transgenic tomato plants with modified levels of ADH2 activity in their ripening fruit. The introduction of the ADH2 cDNA under the control of the constitutive promoter resulted in a spectrum of transformed plants including those with enhanced levels of ADH2 activity in the ripening fruit (and in other tissues, unpublished result) and plants with barely detectable levels of ADH2 activity in the ripening fruit. Transformed plants containing constructs with the tomato PG-promoter, produced fruit showing enhanced levels of the ADH2 activity. In fruit from these plants, ADH2 activity increased as the fruit ripened, consistent with the fruit/ripening specificity of the PG-promoter. No plants containing this construct were found with suppressed ADH2 activity in the ripening fruit, suggesting that pre-existing threshold levels of mRNA must be present before cosuppression of endogenous plus exogenous genes occurs.

Constitutive promoter—high-ADH plant C20

Associated with the increased ADH activity in fruit from plant C20 were increases in the alcohol forms of the hexanol/ol and hexenal/ol volatiles (Table 1) giving rise to reduced ratios of aldehyde to alcohol as seen in FIG. 6. These are consistent with an increased conversion of the C-6 aldehydes to their alcohols by the increased level of ADH in the transformed fruit and is the first direct evidence that the tomato ADH2 enzyme mediates interconversion of hexanal/ol and the Z-3- form of hexenal/ol in the ripening fruit.

Fruit specific promoter—high-ADH plant C13

In fruit from the C13 plant, ADH activity was marginally higher during development, relative to control fruit, but increased to approximately 3 times the level in control fruit, during ripening (FIG. 4). As with the constitutive high-ADH plant C20, an increase in Z-3-hexenol was found in fruit from this plant, resulting in a decrease in hexenal/ol ratios (FIG. 6). However, no increase in hexanol was observed while a decrease in hexanal was evident (Table 1). While this results in the same reduction in aldehyde to alcohol ratio evident in the C20 plant, the mechanism clearly differs, differing also from that mediating the balance between the hexenals and hexenols in both the C13 and C20 plants. Assuming that ADH is involved, the high ADH activity attained in the fruit, or the specific timing of its increase in the tissues may be affecting the mechanism.

Constitutive promoter—low-ADH plant C23

ADH activity was reduced to barely detectable levels in fruit of plant C23. Also barely detectable in these fruit was hexanol and hexenol (Table 1) with the resulting aldehyde to alcohol ratios for C23 fruit differing grossly from those of control fruit (FIG. 6). Reduction of ADH2 activity has therefore resulted in inhibition of the conversion of hexanal and hexenal to their alcohols providing further direct evidence of at least one of the roles of ADH2 in the ripening fruit.

All the transformed plants showing marked modifications of phenotype contained more than one introduced ADH2 construct. The two plants C7 and C14 contained only single insertions (Table 1) and showed only marginal modifications of ADH activity and aldehyde:alcohol ratios. While this suggested a correlation between the number of genes inserted and the magnitude of their effect, the correlation did not hold in all cases. Gene silencing was only observed in plants transformed with constructs regulated by the constitutive promoter and only in plants containing more than one inserted gene (Table 1). The results indicate that modification of ADH2 activity in the tomato fruit affects the regulation of balance between the 6-carbon aldehydes and alcohols.

The tasting trials showed a clear preference by the panelists for fruit from the plant C20. Fruit of this plant showed a statistically significant increase in the alcohols hexanol and 3-Z-hexenol. In order to quantify the increases in these volatiles, simple calculations were made by dividing the hexanol peak area from C20 fruit (Table 1) with that from control fruits. Similar calculations were made using the 3-Z-hexenol peak areas from the two sets of fruit. Such calculations indicated an increase in the amount of hexanol of about 1.2 to 4.6×control fruit and an increase in the amount of 3-Z-hexenol of about 1.5 to 3.7×control fruit.

REFERENCES

1. Flavour Chemistry: Trends and developments (1988). ACS Symposium Series 388, Teranishi R, Buttery R G and Shahidi F eds. American Chemical Society, Washington D.C.
2. Buttery R G, Teranishi R and Ling L C (1987). Fresh Tomato Aroma Volatiles: A Quantitative Study. J. Agric. Food Chem. 35:540–544.
3. buttery R G, Teranishi R, Flath R A and Ling L C (1989). Aroma Development in Ripening Fruit. In: Flavour Chemistry: Trends and Developments. ACS Symposium Series 388. Teranishi R, Buttery R G and Shahidi F eds. American Chemical Society, Washington D.C., pp. 213–222.
4. Dirinck P. De Pooter H and Schamp N (1989). Aroma Development in Ripening Fruit. In: Flavour Chemistry: Trends and developments. ACS Symposium Series 388. Teranishi R, Buttery R G and Shahidi F eds. American Chemical Society, Washington D.C., pp. 23–34.
5. Baldwin E A, Nisperos-Carriedo M O and Moshonas M G (1991). Quantitative Analysis of Flavour and Other Volatiles and for Certain Constituents of Two Tomato Cultivars during Ripening. J. Amer. Soc. Hort. Sci. 116 (2): 265–269.

6. Larsen M and Watkins C B (1995). Firmness and Concentrations of Acetaldehyde, Ethyl Acetate and Ethanol in Strawberries Stored in Controlled and Modified Atmospheres. Postharvest Biology and Technology 5:39–50.
7. Rizzolo A, Lombardi P, Vanoli M and Polesello S (1995). Use of Capillary Gas Chromatography/Sensory Analysis as an Additional Tool for Sampling Technique Comparison in Peach Aroma Analysis. J. High Resol. Chromatogr. 18:309–314.
8. Ulrich D, Eunert S, Hoberg E and Rapp A (1995). Analysis of Strawberry Aroma with Solid Phase Microextraction. Deutsche Lebelsmittel-Rundschau 91(11):349–351.
9. Dirinck, P., Schreyen, L., van Wassenhove, F. and Schamp, N. 1976. Flavour quality of tomatoes. J. Sci. Fd. Agric. 27:499–508.
10. Buttery, R. G., Teranishi, R. and Ling L. C. 1987. Fresh tomato aroma volatiles: A quantitative study. J. Agric. Food Chem. 35:540–544.
11. Yu, M. H., Salunkhe, D. K. and Olsen, L. E. 1968. Production of 3-methyl-butanal from L-leucine by tomato extracts. Plant cell Physiol. 9:633–638.
12. Hatanaka A, Kajiwara T and Sekiya J (1986). Fatty Acid Hyperoxide Lyase in Plant Tissues. Volatile Aldehyde Formation from Linoleic and Linolenic Acid. In: Biogeneration of Aroma. ACS Symposium Series 317. Parliment T H and Croteau R eds. American Chemical Society, Washington D.C. pp. 167–175.
13. Sieso, V., Nicolas, M., Seck, S. and Crouzet, J. 1976. Constituants volatils de la tomate: mise enevidence et formation par voie enzymatique du trans-hexene-2-ol. Agric. Biol. Chem. 40:2349–2353.
14. Bicsak T A, Kann L R, Reiter A and Chase T Jr (1982). Tomato Alcohol Dehydrogenase: Purification and Substrate Specificity. Archives Biochem. Biophys. 216:605–615.
15. Longhurst T J, Tung H F and Brady C J (1990). Developmental Regulation of the Expression of Alcohol Dehydrogenase in Ripening Tomato Fruits. J. Food Biochem. 14:421–433.
16. Chen, A.-R. S. and Chase, T. Jr. 1993. Alcohol dehydrogenase 2 and pyruvate decarboxylase induction in ripening and hypoxic tomato fruit. Plant Physiol. Biochem. 31:875–885.
17. Matzke M A and Matzke A J M (1995). How and Why Do Plants Inactivate Homologous (Trans)genes? Plant Physiology 107:679–685.
18. Homologous Recombination and Gene Silencing in Plants (1994). J Paszkowski (ed.), Kluwer, Dordrecht, The Netherlands.
19. Mechanisms and Applications of Gene Silencing (1996). Grierson D. Lycett G W and Tucker G A (eds.) Nottingham University Press, Nottingham, UK.
20. Longhurst T, Lee L, Hinde R, Brady C and Speirs J (1994). Structure of the Tomato ADH2 Gene and ADH2 Pseudogenes, and a Study of ADH2 Gene Expression in Fruit. Plant Molec. Biol. 26:1073–1084.
21. Smith, G. J. S., Watson, C. F., Ray, J., Bird, C. R., Morris, P. C., Schuch, W. and Grierson, D. 1988. Antisense RNA inhibition of polygalacturonase gene expression in transgenic tomatoes. Nature 334:724–726.
22. Bevan, M. W. 1984. Binary Agrobacterium vectors for plant transformation. Nucl. Acids Res. 12:8711–8721
23. Frisch D A, Harris-Haller L W, Yokubaitis N T, Thomas T L, Hardin S H and Hall T C (1995). Complete Sequence of the Binary Vector Bin 19. Plant Mol. Biol. 27(2):405–409.
24. Nicholass F J, Smith G J S, Schuch W, Bird C R and Grierson D (1995). High Levels of Ripening-Specific Repoter Gene Expression Directed by Tomato Fruit Polygalacturonase Gene-Flanking Regions. Plant Mol. Biol. 28:423–435.
25. Bird C R, Smith C J S, Ray J A, Moureau P, Bevan M J, Birds A S, Hughes S, Morris P C, Grierson D and Schuch W (1988). The tomato polygalacturonase gene and ripening specific expression in transgenic plants. Plants Mol. Biol. 11:651–662.
26. Thomas M R, Matsumoto S, Cain P and Scott N S (1993). Repetitive DNA of Grapevines: Classes Present and Sequences Suitable for Cultivar Idenfication. Theor. Appl. Genet. 86:173–180.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method for producing a transformed fruit plant which produces ripened fruit with improved flavor as compared to ripened fruit produced by its parental plant, said method comprising:

stably transforming explants of said parental plant with at least one DNA molecule comprising a nucleotide sequence encoding alcohol dehydrogenase II (ADH2) operably linked to a suitable promoter sequence, growing transformed fruit plants from said explants, wherein said transformed fruit plants express said DNA molecule(s) in fruit tissue, assessing ripened fruit harvested from said transformed fruit plants for improving flavor, and selecting a transformed fruit plant which produces ripened fruit with improved flavor as compared to ripened fruit produced by said parental plant.

2. A method according to claim 1, wherein the step of selecting a transformed fruit plant which produces ripened fruit with improved flavour, involves selecting a transformed fruit plant which produces fruit which, when ripened, shows a 1 to 10 fold increase in the amounts of the volatile alcohols hexanol and Z-3 hexenol as compared to ripened fruit of said parental plants.

3. A method according to claim 1, wherein the step of selecting a transformed fruit plant which produces ripened fruit with improved flavour, involves selecting a transformed fruit plant which produces fruit which, when ripened, shows a 1 to 5 fold increase in the amounts of the volatile alcohols hexanol and Z-3 hexenol as compared to ripened fruit of said parental plants.

4. A method according to claim 1, wherein the step of selecting a transformed fruit plant which produces ripened fruit with improved flavour, involves selecting a transformed fruit plant which produces fruit which, when ripened, shows a 1.0 to 5.0 fold increase in the amount of hexanol and 1.5 to 4.0 fold increase in the amount of Z-3 hexenol as compared to ripened fruit of said parental plant.

5. A method according to claim 1, wherein the at least one DNA molecule comprises and ADH2 nucleotide sequence which corresponds to the cDNA or genomic sequence shown in FIGS. 1a (SEQ ID NO:1) and 1b (SEQ ID NO:3) respectively.

6. A method according to claim 1, wherein the said suitable promoter sequence is selected from the group consisting of tomato ADH2 promoter, endopolygalacturonase (PG) promoter, 1-aminocyclopropane-1-carboxylic acid oxidase promoter and E8 promoter.

7. A method according to claim 1, wherein the said suitable promoter sequence is a constitutive promoter.

8. A method according to claim 7, wherein the constitutive promoter is selected from the CaMV 35S promoter and SCSV promoters.

9. A method according to claim 1, wherein the fruit plant is a soft fruit plant.

10. A method according to claim 8, wherein the fruit plant is a tomato plant.

11. A fruit plant produced by transforming a parental plant with at least one DNA molecule comprising a nucleotide sequence encoding tomato alcohol dehydrogenase II (ADH2) operably linked to a promoter sequence suitable for expression of the said DNA molecule(s) in fruit tissue, wherein said transformed fruit plant produces ripened fruit with improved fruit flavor as compared to ripened fruit produced by said parental plant.

12. Reproductive tissues derived or produced from a fruit plant according to claim 11.

13. Fruit produced by a fruit plant according to claim 11.

14. A fruit plant according to claim 11, wherein the fruit plant is a soft fruit plant.

15. A fruit plant according to claim 14, wherein the fruit plant is a tomato plant.

16. A plant transformed with at least one DNA molecule comprising a nucleotide sequence which corresponds to the genomic sequence from residue 1-2147 in FIG. 1b (SEQ ID NO:3), said nucleotide sequence encoding tomato ADH2.

17. A plant according to claim 15, wherein the plant has been transformed with multiple copies of a DNA molecule comprising a nucleotide sequence which corresponds to the genomic sequence from residue 1-2147 shown in FIG. 1b (SEQ ID NO:3).

18. An isolated DNA molecule comprising a nucleotide sequence which corresponds to the genomic sequence from residue 1-2147 of FIG. 1b (SEQ ID NO:3) which encodes tomato ADH2.

19. A method according to claim 1, wherein the said at least one DNA molecule comprises a nucleotide sequence encoding ADH2 having the amino acid sequence of SEQ ID NO: 2.

20. A method according to claim 1, wherein the said at least one DNA molecule comprises a nucleotide sequence encoding ADH2 having an N-terminal amino acid sequence of MSTTVGQVIR, corresponding to the first ten amino acids of SEQ ID NO:2.

* * * * *

UNITED STATES PATENT AND TRADEMARK OFFICE
CERTIFICATE OF CORRECTION

PATENT NO. : 6,011,199
DATED : January 04, 2000
INVENTOR(S) : James SPEIRS, et al.

It is certified that error appears in the above-identified patent and that said Letter Patent is hereby corrected as shown below:

On the Title page:

Section [54], in the first inventor's residence, change "Chapham" to --Clapham--.

Section[73], in the assignee's name and address, change "Commonwealth Scientifric; Industrial Research Organisation, both of Campbell, Australia" to -- Commonwealth Scientific and Industrial Research Organisation, Limestone Avenue, Campbell, Australian Capital Territory, 2601, Australia--.

In the Specification:

Column 1, Line 49, delete "(FIG. 1)".

Column 2, Line 2, change "2-carbon" to --6-carbon--.

Line 63, change "who" to --show--.

Column 4, Line 4, change "enhances" to --enhancers--.

Line 62, change "Fig. 1a provides" to --Figs. 1a-1, 1a-2, and 1a-3 provide--.

Line 64, change "Fig. 1b provides" to --Figs. 1b-1, 1b-2, 1b-3 and 1b-4 provide--.

Column 5, Line 18, change "Fig. 3 provides" to --Fig. 3(A)-3(D) provide--.

Line 32, after "point" delete --Ac--.

UNITED STATES PATENT AND TRADEMARK OFFICE
CERTIFICATE OF CORRECTION

Page 2 of 3

PATENT NO. : 6,011,199
DATED : January 04, 2000
INVENTOR(S) : James SPEIRS, et al.

It is certified that error appears in the above-identified patent and that said Letter Patent is hereby corrected as shown below:

Column 5, Line 32, change "in" to --In--.

Figures 4A, 4B, 4C:
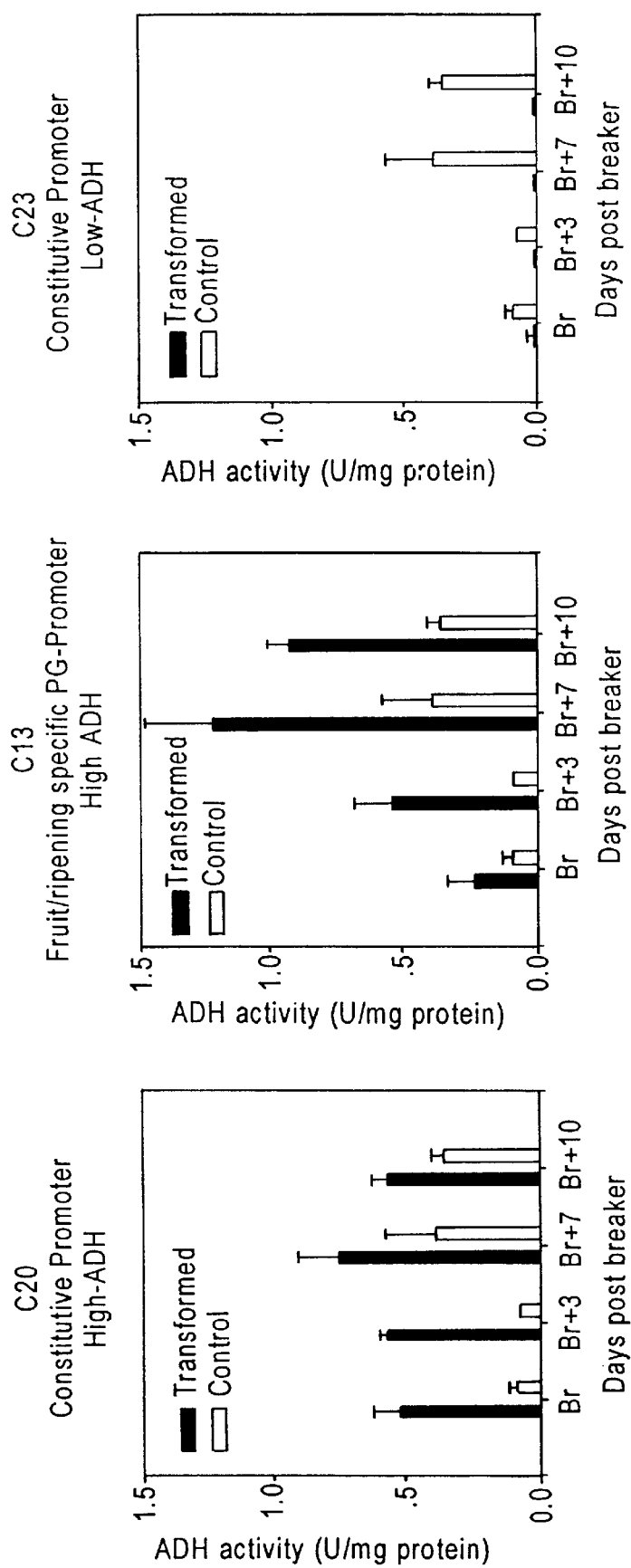

Line 35, change "Fig. 4 provides" to --Figs. 4(A)-4(C) provide--.

Figures 6A, 6B, 6C:
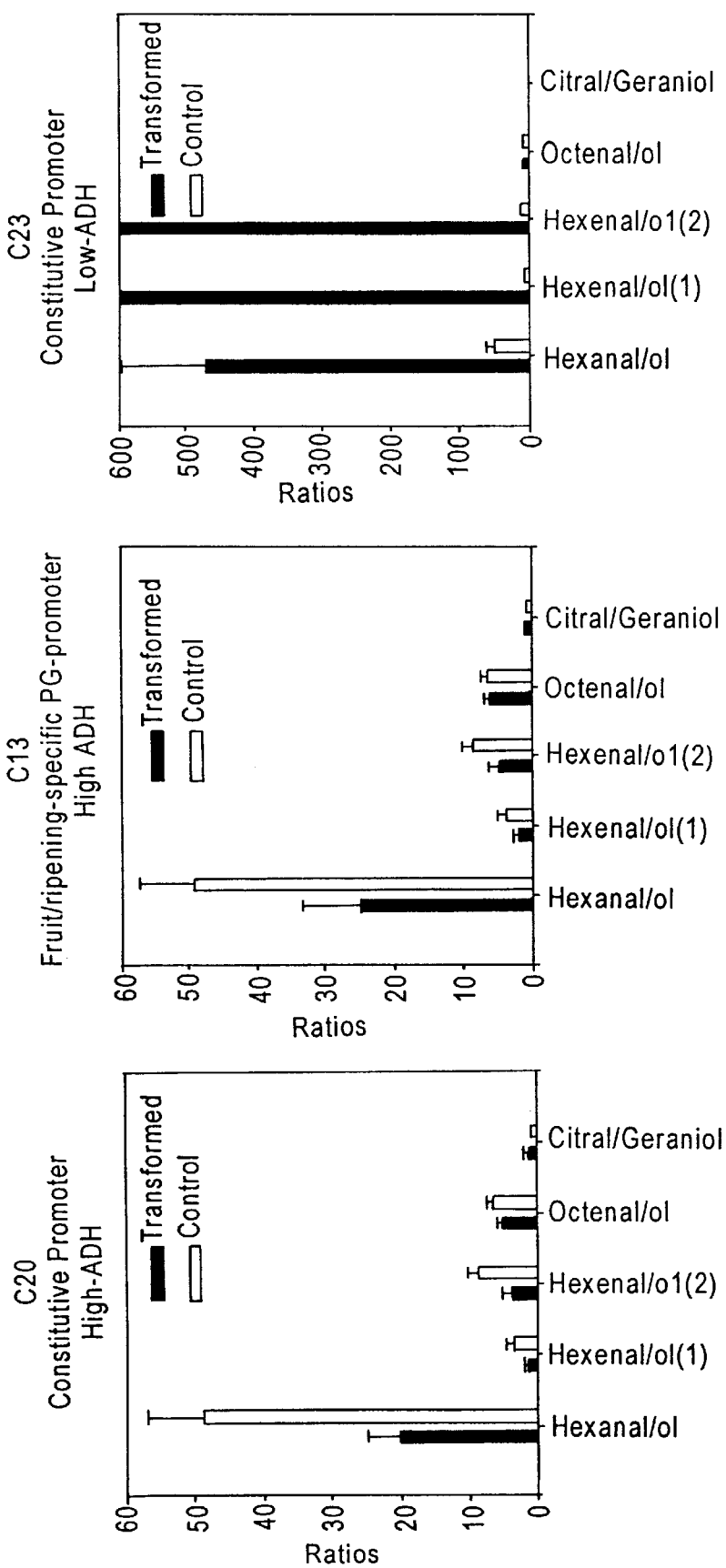

Line 49, change "Fig. 6 provides" to --Figs. 6(A)-6(C) provide--.

Column 6, Line 18, change "or" to --of--.

Line 38, change "BGI11" to --BglI--.

Line 39, after "genomic" delete --of--.

Line 39, change "cDNA" to --DNA--.

Line 45, should read --library, encoded the tomato ADH2 enzyme--.

Column 7, Line 2, change "as" to --was--.

Column 9, Line 12, change "32p" to --$^{32}$P--.

Column 10, Line 8, change "is" to --i.e.--.

Line 35, after "to" delete --a--.

UNITED STATES PATENT AND TRADEMARK OFFICE
CERTIFICATE OF CORRECTION

PATENT NO. : 6,011,199
DATED : January 04, 2000
INVENTOR(S) : James SPEIRS, et al.

It is certified that error appears in the above-identified patent and that said Letter Patent is hereby corrected as shown below:

Column 14, Line 52, change "buttery" to --Buttery--.

In the Claims:

Column 33, Claim 1, Line 34, change "improving" to --improved--.

Claim 5, Line 59, change "and" to --an--.

Signed and Sealed this

Twenty-fourth Day of April, 2001

*Attest:*

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 1520 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
AAATATCCAC TGCCTCAACT GAGTAAACAA CCAAAATTTG TGTTCTATAA AAAGTTTTCA        60

TATTTAGTGA TCACTAAAAA AAAATCAAGA AGATGTCGAC TACTGTAGGC CAAGTCATTC       120
```

-continued

```
GTTGCAAAGC TGCTGTGGCA TGGGAGGCTG GTAAGCCATT AGTGATGGAG GAAGTGGATG      180

TTGCTCCTCC ACAGAAAATG GAAGTTCGTC TTAAGATCCT CTACACTTCA CTCTGTCATA      240

CTGATGTATA CTTCTGGGAA GCTAAGGGTC AAAATCCAGT CTTTCCTCGA ATTCTTGGAC      300

ATGAAGCAGC AGGGATTGTG GAGAGTGTTG GAGAGGGAGT AACAGACCTT GCACCAGGAG      360

ACCATGTTCT TCCTGTCTTT ACAGGGGAAT GTAAAGATTG CGCTCACTGT AAATCTGAAG      420

AAAGCAATAT GTGTAGCCTC TTAAGGATTA ACACTGACAG GGGAGTGATG CTTAATGATG      480

GAAAATCAAG ATTTTCCATC AATGGAAACC CCATTTACCA TTTTGTTGGG ACCTCTACTT      540

TTAGTGAGTA CACCGTGGTT CATGTTGGAT GTGTTGCAAA AATTAACCCT CTTGCTCCTC      600

TTGACAAAGT ATGTGTCCTT AGTTGTGGAA TTTCGACAGG CCTTGGAGCA AGTTTGAATG      660

TTGCTAAACC AACAAAAGGC TCAAGTGTGG CTATATTTGG ACTAGGAGCT GTAGGCCTCG      720

CGGCTGCAGA AGGAGCCAGA ATTGCTGGTG CCTCGAGGAT AATTGGTGTT GATTTAAATG      780

CTAGTAGATT TGAGCAAGCT AAGAAATTTG GTGTGACAGA GTTTGTGAAC CCAAAGGACT      840

ATAGTAAACC AGTTCAAGAG GTAATTGCTG AGATGACTGA TGGCGGAGTC GATAGGAGTG      900

TGGAATGTAC TGGTCACATT GATGCTATGA TTTCAGCATT TGAATGTGTC CATGATGGCT      960

GGGGAGTGGC GGTTCTTGTT GGTGTACCCC ATAAAGAAGC TGTGTTCAAG ACACATCCTC     1020

TGAACTTTTT GAATGAACGG ACTCTCAAAG GAACCTTCTT TGGAAACTAC AAACCTCGTT     1080

CGGATATTCC TTGTGTTGTT GAGAAATACA TGAACAAAGA ACTTGAATTG GAGAAATTCA     1140

TCACTCATAC ACTTCCATTT GCTGAAATCA ATAAGGCTTT CGATTTAATG CTGAAGGGAG     1200

AAGGCCTTCG TTGCATCATC ACCATGGCGG ACTAAACTTT CTGTCCTAGA AAAGGAGCTT     1260

CTACTGTTTA AGAAAAAGA CCAATAAATT GTCACTGTCT TATTTTCCCT TTCGTGTTTG     1320

GTTGAGTTGT AACATTCCAT CCATGTCTCT TCTTTTGTCT TTTGCTTAGA TGTTGTGCTT     1380

TGCCATATCT CTTTCGATTC TTGTAAAAAA TGCAAATTCT CTCTGTTTTA TCTCAAGTAT     1440

ATTTACAGAA TTTCAGTGAT TGATAAATC TAAACTTTAT CATAATATAA TCCAAACAGA      1500

ATTTCAATTG AAAAAAAAAA                                                 1520
```

(2) INFORMATION FOR SEQ ID NO:2:

(i) SEQUENCE CHARACTERISTICS:
        (A) LENGTH: 379 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ser Thr Thr Val Gly Gln Val Ile Arg Cys Lys Ala Ala Val Ala
1               5                  10                  15

Trp Glu Ala Gly Lys Pro Leu Val Met Glu Glu Val Asp Val Ala Pro
            20                  25                  30

Pro Gln Lys Met Glu Val Arg Leu Lys Ile Leu Tyr Thr Ser Leu Cys
        35                  40                  45

His Thr Asp Val Tyr Phe Trp Glu Ala Lys Gly Gln Asn Pro Val Phe
    50                  55                  60

Pro Arg Ile Leu Gly His Glu Ala Ala Gly Ile Val Glu Ser Val Gly
65                  70                  75                  80

Glu Gly Val Thr Asp Leu Ala Pro Gly Asp His Val Leu Pro Val Phe
                85                  90                  95
```

```
Thr Gly Glu Cys Lys Asp Cys Ala His Cys Lys Ser Glu Glu Ser Asn
            100                 105                 110

Met Cys Ser Leu Leu Arg Ile Asn Thr Asp Arg Gly Val Met Leu Asn
            115                 120                 125

Asp Gly Lys Ser Arg Phe Ser Ile Asn Gly Asn Pro Ile Tyr His Phe
130                 135                 140

Val Gly Thr Ser Thr Phe Ser Glu Tyr Thr Val Val His Val Gly Cys
145                 150                 155                 160

Val Ala Lys Ile Asn Pro Leu Ala Pro Leu Asp Lys Val Cys Val Leu
                165                 170                 175

Ser Cys Gly Ile Ser Thr Gly Leu Gly Ala Ser Leu Asn Val Ala Lys
            180                 185                 190

Pro Thr Lys Gly Ser Ser Val Ala Ile Phe Gly Leu Gly Ala Val Gly
            195                 200                 205

Leu Ala Ala Ala Glu Gly Ala Arg Ile Ala Gly Ala Ser Arg Ile Ile
210                 215                 220

Gly Val Asp Leu Asn Ala Ser Arg Phe Glu Gln Ala Lys Lys Phe Gly
225                 230                 235                 240

Val Thr Glu Phe Val Asn Pro Lys Asp Tyr Ser Lys Pro Val Gln Glu
                245                 250                 255

Val Ile Ala Glu Met Thr Asp Gly Gly Val Asp Arg Ser Val Glu Cys
            260                 265                 270

Thr Gly His Ile Asp Ala Met Ile Ser Ala Phe Glu Cys Val His Asp
            275                 280                 285

Gly Trp Gly Val Ala Val Leu Val Gly Val Pro His Lys Glu Ala Val
            290                 295                 300

Phe Lys Thr His Pro Leu Asn Phe Leu Asn Glu Arg Thr Leu Lys Gly
305                 310                 315                 320

Thr Phe Phe Gly Asn Tyr Lys Arg Ser Asp Ile Pro Cys Val Val Glu
                325                 330                 335

Lys Tyr Met Asn Lys Glu Leu Glu Leu Glu Lys Phe Ile Thr His Thr
            340                 345                 350

Leu Pro Phe Ala Glu Ile Asn Lys Ala Phe Asp Phe Met Leu Lys Gly
            355                 360                 365

Glu Gly Leu Arg Cys Ile Ile Thr Met Ala Asp
370                 375

(2) INFORMATION FOR SEQ ID NO:3:

(i) SEQUENCE CHARACTERISTICS:
        (A) LENGTH: 3088 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GATCAAAAGA TGAACTAAGG ATAATATTTT TGATATTTTA CCTTTTTTTT AATTATAACG      60

TTGTTAAGAT ATCAAAGGAC CAATTATAAG AAAACCACCC AAAGGTTTCA TGTTTTGATT     120

GAAAAAACCA TCAAACAACG CAATACAACT GCTCAACTAG AATCAACATA ACAAAAAAAT     180

ATACTTAATG AGATCATTTA TAACCTAAAT TATAACCCCT CCGTGCACTT TCATTTATCA     240

TGTTATATTT TACGCAAGTC AATTTGATTC ATTTTAAAAG TTAAATGAGA TTATATTAAT     300

TTAATATTTT AAATAAAATT TTCAGATATT TAAAAATTAT ATGAAAAGTA TCATGAATTG     360

TAGTTTTTTT TTGCATATAT GAAAAAATAC ATTATAAATA TTAGTCAATT TTTTTATAAT     420
```

```
TTGACTCTAA ATATGAAAAA AAATGACAAT TAAAAATAGA CGGAGGTTGT AAATTAGCTT      480

ATTAATTATT AATTTGATAA ATATCATAAT TAACTGATAA TGACAATTAA ATATTTAGAA      540

GACGATAATG ACAGAAATCA ACGTTATTTT AGGTATAATT TTTGTTGTAT TTTTGAAAAA      600

AATAATCTTT TTTCTGCAAC TGGTTATATT AAGTGAACAA ACAAAAAACA AGTAGTATAA      660

AAAAATTACA AGTGGACATA AAACAAAATG AGATACAGTA TTTGTGTTTC CATTGGAATA      720

TTAGCTTGAC AAAAACTCAA ACGAGCAACA CAAAACAAAC AGCTAAAAAA CCTGTTTTGA      780

AAAATCCAGT GACCAAAACA TGTAAATGGT TTTACTGTGG CCTATTGTTT TTTCACCTTT      840

CCCAATTATA AATATCCACT GCCTCAACTG AGTAAACAAC CAAAATTTGT GTTCTATAAA      900

AAGTTTTCAT ATTTAGTGAT CACTAAAAAA AAATCAAGAA GATGTCGACT ACTGTAGGCC      960

AAGTCATTCG TTGCAAAGGT ATAATAATTC CATGATTCTG TAATTTCCTC GTTTTTTTTT     1020

TTAAGTTTGA TAATTTTTGT GGTAATTATA TATTATTTAT AGCTGCTGTG GCATGGGAAG     1080

CTGGTAAGCC ATTAGTGATG GAGGAAGTAG ATGTTGCTCC TCCACAGAAA ATGGAAGTTC     1140

GTCTTAAGAT CCTCTATACT TCACTCTGTC ATACTGATGT ATACTTCTGG GAAGCTAAGG     1200

TAAACAAAAC TAAATTACGG GACTACGTTG AGTATGTTAG TGTTGTCAGC AAATTTTATA     1260

AGGGGATTAT TTCCTTTGAA CTGATTTCAG GGTCAAAATC CAGTCTTTCC TCGAATTCTT     1320

GGACATGAAG CAGCAGGGTA TGTGTTATCT TGTTTCAATT GATTGATTTG AATTCATCAT     1380

TTACTGTTTC TAAAGCTAAA AGGGTACTGA ATTTTGTTGT CTTCTTGATA TTTAGGATTG     1440

TGGAGAGTGT TGGAGAGGGA GTAACAGACC TTGCACCAGG AGACCATGTT CTTCCTGTCT     1500

TTACAGGGGA ATGTAAAGAT TGTGCTCACT GTAAATCTGA AGAAAGCAAT ATGTGTAGCC     1560

TCTTAAGGAT TAACACTGAC AGGGGAGTGA TGCTTAATGA TGGAAAATCA AGATTTTCCA     1620

TCAATGGAAA CCCCATTTAC CATTTTGTTG GGACCTCTAC TTTTAGTGAG TACACCGTGG     1680

TTCATGTTGG ATGTGTTGCA AAAATTAACC CTCTTGCTCC TCTTGACAAA GTATGTGTCC     1740

TTAGTTGTGG AATTTCGACA GGTATAGACG AAGACAACGA TAGATTATGT TACTAGTTTC     1800

TTTTTAAGGA GCTGCTCAAT TGTTGATTGA TATGAATACT TTTCCAGGCC TTGGAGCAAG     1860

TTTGAATGTT GCTAAACCAA CAAAAGGCTC AAGTGTGGCT ATATTTGGAC TAGGAGCTGT     1920

AGGCCTCGCG GTGAGTATGC TCCGTTGTGT TGTTTTATTG TTTCCCGTAT ATGTGTTAGT     1980

CTTACAGATG ACTGACTCAT TTGGTCAGGC TGCAGAAGGA GCCAGAATTG CTGGTGCCTC     2040

GAGGATAATT GGTGTTGATT TAAATGCTAG TAGATTTGAG CAAGGTAATA TAAATTTTTC     2100

CTTATACATT ATCTTAAAAT TCCTTAGTAA AACAACTAAT TCATCCATTT TACTTGTATT     2160

CTACAGCTAA GAAATTTGGT GTGACAGAGT TTGTGAACCC AAAGGACTAT AGTAAACCAG     2220

TTCAAGAGGT ACTCAAATCA TATTTAATTT ACTTTAATCG AAGAAGAAAA AAGACAGGTC     2280

TGAGTTAATA GTTGATGTCT TTTCTTGAAT TCTGATTATT TGATCAGGTA ATTGCTGAGA     2340

TGACTGATGG CGGAGTCGAT AGGAGTGTGG AATGTACGGG TCACATTGAT GCTATGATTT     2400

CAGCATTTGA ATGTGTCCAT GATGTATGTT TTCTGTAATC AAATTAATTT CCTTAGCTGT     2460

ATGTTTGCGT TCATCTTAAC GAACATTGTT GTATTAACTT TAGGGCTGGG GAGTCGCGGT     2520

TCTTGTTGGT GTACCCCATA AAGAAGCTGT GTTCAAGACA CATCCTCTGA ACTTTTTGAA     2580

TGAACGGACT CTCAAAGGAA CCTTCTTTGG AAACTACAAA CCTCGTTCGG ATATTCCTTG     2640

TGTTGTTGAG AAATACATGA ACAAAGAACT TGAATTGGAG AAATTCATCA CTCATACACT     2700

TCCATTTGCT GAAATCAATA AGGCTTTCGA TTTAATGCTG AAGGGAGAAG GCCTTCGTTG     2760

CATCATCACC ATGGCGGACT AAACTTTCTG TCCTAGAAAA GGAGCTTCTA CTGTTTGAGA     2820
```

```
AAAAAGACCA ATAAATTGTC ACTGTCTTAT TTTCCCTTTC GTGTTTGGTT GAGTTGTAAC    2880

ATTCCATCCA TGTCTCTTCT TTTGTCTTTT GCTTAGATGT TGTGCTTTGC CATATCTCTT    2940

TCGATTCTTG TAAAAAATGC AAATTCTCTC TGTTTTATCT CAAGTATATT TACAGAATTT    3000

CAGTGATTTG ATAAATCTAA ACTTTATCAT AATATAATCC AAACAGAATT TCAATTGAAA    3060

ATGATGAAGC CCTTACCGTC ATTGTTCC                                       3088
```

(2) INFORMATION FOR SEQ ID NO:4:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
AAATATCCAC TGCCTCAACT GAGTAAACAA CCAAAATTTG TGTTCTATAA AAAGTTTTCA     60

TATTTAGTGA TCACTAAAAA AAAATCAAGA AGATGTCGAC TACTGTAGGC CAAGTCATTC    120

GTTGCAAAG                                                            129
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Ser Thr Thr Val Gly Gln Val Ile Arg Cys Lys
 1               5                  10
```

(2) INFORMATION FOR SEQ ID NO:6:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CTGCTGTGGC ATGGGAAGCT GGTAAGCCAT TAGTGATGGA GGAAGTAGAT GTTGCTCCTC     60

CACAGAAAAT GGAAGTTCGT CTTAAGATCC TCTATACTTC ACTCTGTCAT ACTGATGTAT    120

ACTTCTGGGA AGCTAAG                                                   137
```

(2) INFORMATION FOR SEQ ID NO:7:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Ala Ala Val Ala Trp Glu Ala Gly Lys Pro Leu Val Met Glu Glu Val
 1               5                  10                  15
```

```
Asp Val Ala Pro Pro Gln Lys Met Glu Val Arg Leu Lys Ile Leu Tyr
            20                  25                  30

Thr Ser Leu Cys His Thr Asp Val Tyr Phe Trp Glu Ala Lys
        35                  40                  45
```

(2) INFORMATION FOR SEQ ID NO:8:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GGTCAAAATC CAGTCTTTCC TCGAATTCTT GGACATGAAG CAGCAGG              47
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Gly Gln Asn Pro Val Phe Pro Arg Ile Leu Gly His Glu Ala Ala Gly
1               5                   10                  15
```

(2) INFORMATION FOR SEQ ID NO:10:

(i) SEQUENCE CHARACTERISTICS:
        (A) LENGTH: 326 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GATTGTGGAG AGTGTTGGAG AGGGAGTAAC AGACCTTGCA CCAGGAGACC ATGTTCTTCC     60

TGTCTTTACA GGGGAATGTA AAGATTGCGC TCACTGTAAA TCTGAAGAAA GCAATATGTG   120

TAGCCTCTTA AGGATTAACA CTGACAGGGG AGTGATGCTT AATGATGGAA AATCAAGATT   180

TTCCATCAAT GGAAACCCCA TTTACCATTT TGTTGGGACC TCTACTTTTA GTGAGTACAC   240

CGTGGTTCAT GTTGGATGTG TTGCAAAAAT TAACCCTCTT GCTCCTCTTG ACAAAGTATG   300

TGTCCTTAGT TGTGGAATTT CGACAG                                        326
```

(2) INFORMATION FOR SEQ ID NO:11:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Ile Val Glu Ser Val Gly Glu Gly Val Thr Asp Leu Ala Pro Gly Asp
1               5                   10                  15
```

```
His Val Leu Pro Val Phe Thr Gly Glu Cys Lys Asp Cys Ala His Cys
            20                  25                  30

Lys Ser Glu Glu Ser Asn Met Cys Ser Leu Leu Arg Ile Asn Thr Asp
        35                  40                  45

Arg Gly Val Met Leu Asn Asp Gly Lys Ser Arg Phe Gly Ile Asn Gly
    50                  55                  60

Asn Pro Ile Tyr His Phe Val Gly Thr Ser Thr Phe Ser Glu Tyr Thr
65                  70                  75                  80

Val Val His Val Gly Cys Val Ala Lys Ile Asn Pro Leu Ala Pro Leu
                85                  90                  95

Asp Lys Val Cys Val Leu Ser Cys Gly Ile Ser Thr
            100                 105
```

(2) INFORMATION FOR SEQ ID NO:12:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GCCTTGGAGC AAGTTTGAAT GTTGCTAAAC CAACAAAAGG CTCAAGTGTG GCTATATTTG      60

GACTAGGAGC TGTAGGCCTC GCG                                             83
```

(2) INFORMATION FOR SEQ ID NO:13:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Gly Leu Gly Ala Ser Leu Asn Val Ala Lys Pro Thr Lys Gly Ser Ser
1               5                   10                  15

Val Ala Ile Phe Gly Leu Gly Ala Val Gly Leu Ala
            20                  25
```

(2) INFORMATION FOR SEQ ID NO:14:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
GCTGCAGAAG GAGCCAGAAT TGCTGGTGCC TCGAGGATAA TTGGTGTTGA TTTAAATGCT      60

AGTAGATTTG AGCAAG                                                     76
```

(2) INFORMATION FOR SEQ ID NO:15:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Ala Ala Glu Gly Ala Arg Ile Ala Gly Ala Ser Arg Ile Ile Gly Val
1               5                  10                  15

Asp Leu Asn Ala Ser Arg Phe Glu Gln
            20                  25

(2) INFORMATION FOR SEQ ID NO:16:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CTAAGAAATT TGGTGTGACA GAGTTTGTGA ACCCAAAGGA CTATAGTAAA CCAGTTCAAG      60

AG                                                                   62

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Ala Lys Lys Phe Gly Val Thr Glu Phe Val Asn Pro Lys Asp Tyr Ser
1               5                  10                  15

Lys Pro Val Gln Glu
            20

(2) INFORMATION FOR SEQ ID NO:18:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GTAATTGCTG AGATGACTGA TGGCGGAGTC GATAGGAGTG TGGAATGTAC TGGTCACATT      60

GATGCTATGA TTTCAGCATT TGAATGTGTC CATGATG                              97

(2) INFORMATION FOR SEQ ID NO:19:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

Val Ile Ala Glu Met Thr Asp Gly Gly Val Asp Arg Ser Val Glu Cys
1               5                  10                  15

```
     Thr Gly His Ile Asp Ala Met Ile Ser Ala Phe Glu Cys Val His Asp
              20                  25                  30
```

(2) INFORMATION FOR SEQ ID NO:20:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
GCTGGGGAGT GGCGGTTCTT GTTGGTGTAC CCCATAAAGA AGCTGTGTTC AAGACACATC    60

CTCTGAACTT TTTGAATGAA CGGACTCTCA AAGGAACCTT CTTTGGAAAC TACAAACCTC   120

GTTCGGATAT TCCTTGTGTT GTTGAGAAAT ACATGAACAA AGAACTTGAA TTGGAGAAAT   180

TCATCACTCA TACACTTCCA TTTGCTGAAA TCAATAAGGC TTTCGATTTA ATGCTGAAGG   240

GAGAAGGCCT TCGTTGCATC ATCACCATGG CGGACTAAAC TTTCTGTCCT AGAAAAGGAG   300

CTTCTACTGT TTGAGAAAAA AGACCAATAA ATTGTCACTG TCTTATTTTC CCTTTCGTGT   360

TTGGTTGAGT TGTAACATTC CATCCATGTC TCTTCTTTTG TCTTTTGCTT AGATGTTGTG   420

CTTTGCCATA TCTCTTTCGA TTCTTGTAAA AAATGCAAAT TCTCTCTGTT TTATCTCAAG   480

TATATTTACA GAATTTCAGT GATTTGATAA ATCTAAACTT TATCATAATA TAATCCAAAC   540

AGAATTTCAA TTGAAAAAAA                                               560
```

(2) INFORMATION FOR SEQ ID NO:21:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Gly Trp Gly Val Ala Val Leu Val Gly Val Pro His Lys Glu Ala Val
1               5                   10                  15

Phe Lys Thr His Pro Leu Asn Phe Leu Asn Glu Arg Thr Leu Lys Gly
                20                  25                  30

Thr Phe Phe Gly Asn Tyr Lys Pro Arg Ser Asp Ile Pro Cys Val Val
            35                  40                  45

Glu Lys Tyr Met Asn Lys Glu Leu Glu Leu Glu Lys Phe Ile Thr His
        50                  55                  60

Thr Leu Pro Phe Ala Glu Ile Asn Lys Ala Phe Asp Leu Met Leu Lys
65                  70                  75                  80

Gly Glu Gly Leu Arg Cys Ile Ile Thr Met Ala Asp
                85                  90
```

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO:22:

CCACTGCCTC AACTGAG                                                    17

(2) INFORMATION FOR SEQ ID NO:23:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:23:

ACTAATGGCT TACCAGC                                                    17
```